US010265374B2

(12) United States Patent
Smith et al.

(10) Patent No.: US 10,265,374 B2
(45) Date of Patent: Apr. 23, 2019

(54) OCCIDIOFUNGIN FORMATIONS AND USES THEREOF

(71) Applicants: MISSISSIPPI STATE UNIVERSITY, Starkville, MS (US); THE TEXAS A&M UNIVERSITY SYSTEM, College Station, TX (US)

(72) Inventors: James L. Smith, College Station, TX (US); Stephen Pruett, Starkville, MS (US); Frank Austin, Starkville, MS (US); Shien Lu, Starkville, MS (US); Ravichandran Akshaya, Bryan, TX (US); Steven Laihing, College Station, TX (US)

(73) Assignees: MISSISSIPPI STATE UNIVERSITY, Starkville, MS (US); THE TEXAS A&M UNIVERSITY SYSTEM, College Station, TX (US)

( * ) Notice: Subject to any disclaimer, the term of this patent is extended or adjusted under 35 U.S.C. 154(b) by 28 days.

(21) Appl. No.: 15/510,801

(22) PCT Filed: Sep. 14, 2015

(86) PCT No.: PCT/US2015/049972
§ 371 (c)(1),
(2) Date: Mar. 13, 2017

(87) PCT Pub. No.: WO2016/040940
PCT Pub. Date: Mar. 17, 2016

(65) Prior Publication Data
US 2017/0281721 A1    Oct. 5, 2017

Related U.S. Application Data

(60) Provisional application No. 62/049,788, filed on Sep. 12, 2014.

(51) Int. Cl.
| A61K 38/12 | (2006.01) |
|---|---|
| A61K 45/06 | (2006.01) |
| A61K 47/40 | (2006.01) |
| A61K 9/00 | (2006.01) |
| A61K 9/08 | (2006.01) |
| A61K 9/127 | (2006.01) |
| A61K 31/724 | (2006.01) |

(52) U.S. Cl.
CPC ............ *A61K 38/12* (2013.01); *A61K 9/0019* (2013.01); *A61K 9/08* (2013.01); *A61K 9/127* (2013.01); *A61K 31/724* (2013.01); *A61K 45/06* (2013.01); *A61K 47/40* (2013.01)

(58) Field of Classification Search
None
See application file for complete search history.

(56) References Cited

U.S. PATENT DOCUMENTS

| 8,785,376 | B2 | 7/2014 | Schmidt et al. |
|---|---|---|---|
| 9,139,616 | B2 | 9/2015 | Schmidt et al. |
| 9,614,270 | B2 | 4/2017 | Smith et al. |
| 9,879,048 | B2 | 1/2018 | Schmidt et al. |
| 2003/0130121 | A1 | 7/2003 | Gerhardson et al. |
| 2004/0209325 | A1 | 10/2004 | Yang et al. |
| 2005/0026819 | A1 | 2/2005 | Kaniga |
| 2006/0003944 | A1 | 1/2006 | Glinka et al. |
| 2006/0229432 | A1 | 10/2006 | Danishefsky et al. |
| 2007/0202051 | A1 | 8/2007 | Schuschnig |
| 2011/0002983 | A1 | 1/2011 | Hipler et al. |
| 2011/0045037 | A1 | 2/2011 | Tamarkin et al. |
| 2011/0136729 | A1 | 6/2011 | Lu et al. |
| 2015/0024998 | A1 | 1/2015 | Schmidt et al. |

FOREIGN PATENT DOCUMENTS

| EP | 2925774 B1 | 1/2018 |
|---|---|---|
| WO | 20110162830 A2 | 12/2011 |
| WO | WO2013096697 A3 | 6/2013 |
| WO | WO2014085419 A1 | 6/2014 |
| WO | WO2016040940 A1 | 3/2016 |

OTHER PUBLICATIONS

Loftsson et al., "Pharmaceutical Applications of Cyclodextrins. 1. Drug Solubilization and Stabilization," J. Pharma. Sci. 85:1017-1025 (1996).*
Challa et al., "Cyclodextrins in Drug Delivery: An Updated Review," AAPS PharmSciTech 6:E329-E357 (2005).*
Song et al., "The Antifungal Drug Clotrimazole," Acta Cryst. C54:1675-1677 (1998).*
Chang et al., "Clinical development of liposome-based drugs: formulation, characterization, and therapeutic, efficacy," Int. J. Nanomed. 7: 49-60 (2012).*
Akers et al., "Peptides and Proteins as Parenteral Solutions," Pharmaceutical Formulation Development of Peptides and Proteins, Hovgaard ed., CRC Press, Chptr. 8, pp. 149-192 (2012).*
Brewster, Marcus E., and Thorsteinn Loftsson. "Cyclodextrins as pharmaceutical solubilizers." Advanced drug delivery reviews 59.7 (2007): 645-666.
Hing, Steven Lai, et al. "Toxicological evaluation of occidiofungin against mice and human cancer cell lines." Pharmacology & Pharmacy 5.11 (2014): 1085.

(Continued)

*Primary Examiner* — Julie Ha
*Assistant Examiner* — Kristina M Hellman
(74) *Attorney, Agent, or Firm* — Mendelsohn Dunleavy, P.C.

(57) ABSTRACT

Disclosed are occidiofungin formulations and uses thereof for the treatment of proliferative disorders, such as cancer. Methods of producing the disclosed occidiofungin formulations are also provided. Further, methods of treating a subject with the formulations are provided. In some embodiments, the formulations include occidiofungin and one or more cyclodextrins. The formulations may optionally further comprise an additional chemotherapeutic agent for treating the proliferative disease, lipid vesicles, and/or aqueous solvents (including pharmaceutically acceptable buffers and/or exceipients).

44 Claims, 7 Drawing Sheets

(56) References Cited

OTHER PUBLICATIONS

Lu, S-E., Woolfolk, S., and Caceres, J. (2005) Isolation and identification and genetic analysis of rhizobacteria antagonistic to plant soilborne fungal pathogens. Phytopathology 95, 62-61.
Gu, G., Wang, N., Chaney, N., Smith, L., and Lu, S-E. (2009) AmbR1 is a key transcriptional regulator for production of antifungal activity of Burkholderia contaminans strain MS14. FEMS Microbiol. Lett. Accepted May 5, 2009.

Gu, G. Y., Smith, L, Wang, N., Wang, H., and Lu, S-E. (2009) Biosynthesis of an antifungal oligopeptide in Burkholderia contaminans strain MS14. Biochem. Biophys. Res. Commun. 380, 328-332.

Ghannoum, M. G., and Rice, L. B. (1999) Antifungal Agents: Mode of Action, Mechanisms of Resistance, and Correlation of these Mechanisms with Bacterial Resistance. 5 Clin. Microbiol. Rev. 12, 501-517.

* cited by examiner

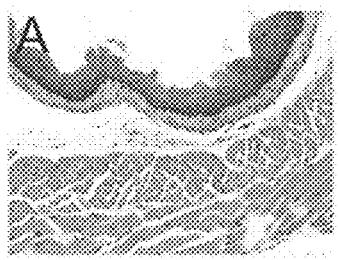 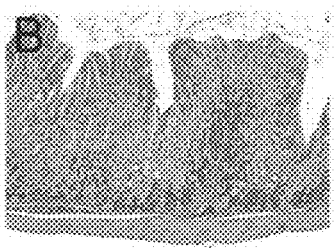 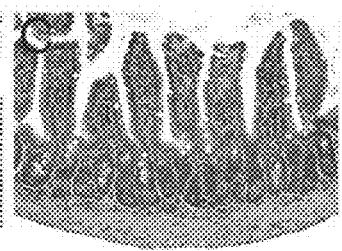
FIG. 2A   FIG. 2B   FIG. 2C
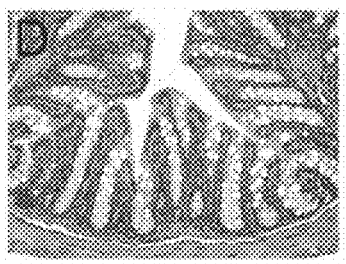 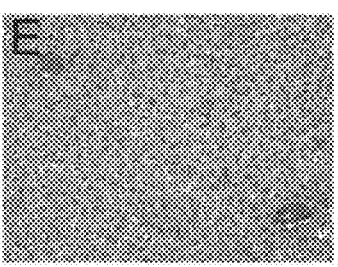 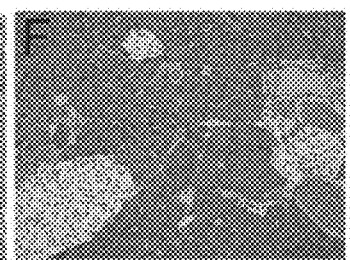
FIG. 2D   FIG. 2E   FIG. 2F
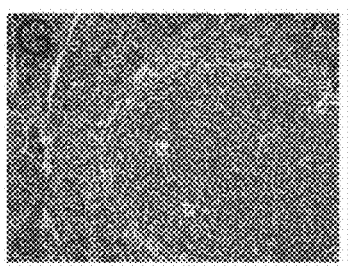 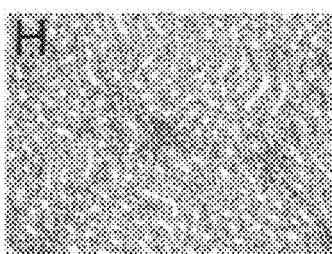 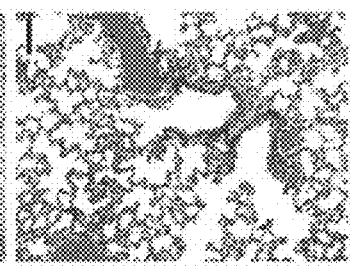
FIG. 2G   FIG. 2H   FIG. 2I
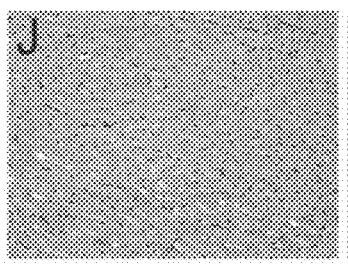 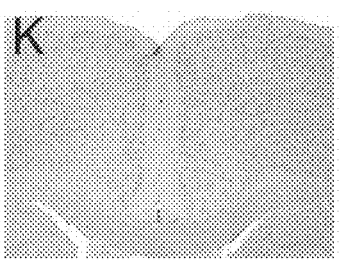 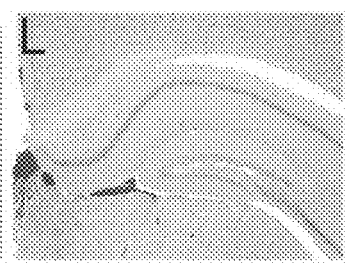
FIG. 2J   FIG. 2K   FIG. 2L

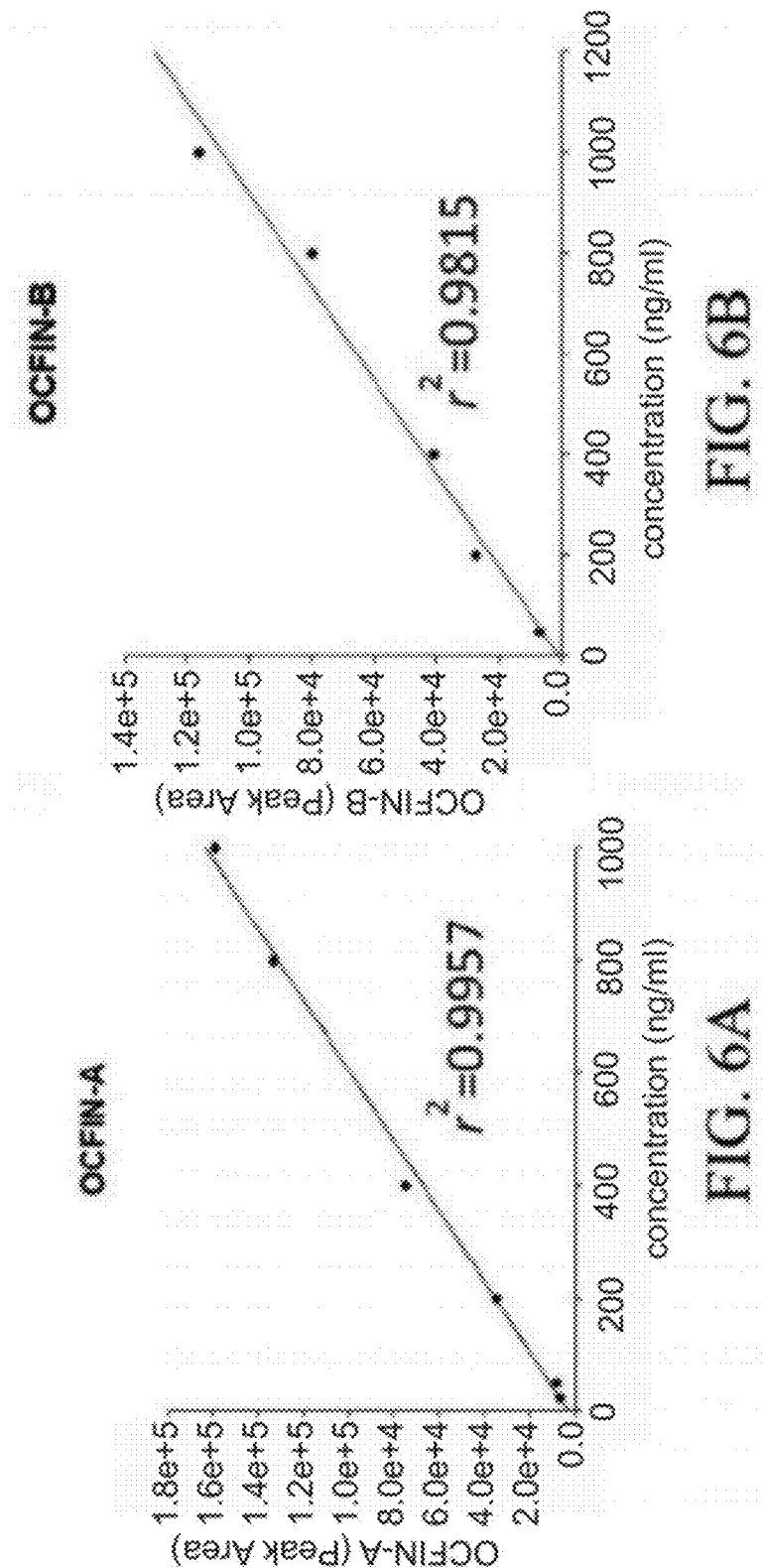

OCCIDIOFUNGIN FORMATIONS AND USES THEREOF

CROSS-REFERENCES TO RELATED APPLICATIONS

This application is a national stage application under 35 U.S.C. § 371 of International Patent Application No. PCT/US2015/049972, filed on Sep. 14, 2015 which claims the benefit of U.S. Provisional Application No. 62/049,788, filed Sep. 12, 2014, both of which are incorporated herein by reference in their entirety.

STATEMENT REGARDING FEDERALLY SPONSORED RESEARCH OR DEVELOPMENT

This invention was made with government support under 232594 awarded by the National Institute of Food and Agriculture, USDA. The U.S. government has certain rights in the invention.

FIELD OF THE INVENTION

The present invention relates generally to therapeutic formulations comprising occidiofungin. In greater particularity, the present invention relates to therapeutic formulations comprising occidiofungin useful for treating cancer.

BACKGROUND OF THE INVENTION

Occidiofungin is a compound purified from liquid culture of *Burkholderia contaminans* MS14 (See References 1-8). The compound is a non-ribosomally synthesized cyclic peptide, composed of eight amino acids, having a base mass of about 1200 Da (FIG. 1). An eighteen carbon fatty amino acid with a xylose sugar attached was identified in the compound, along with non proteinogenic amino acids 2,4-diaminobutyric acid (DABA), and beta hydroxyl tyrosine and asparagine. Biological activity assays demonstrated its potent antifungal properties against a broad spectrum of plant and animal fungal pathogens (See References 1, 2, 7, 8). Pharmacodynamic experiments revealed that occidiofungin's fungicidal activity against *Candida albicans* is more rapid than the fungicidal activity reported for the echinocandin antifungal caspofungin (See References 9, 10).

Cancers are among the leading causes of lost productivity and death in developed nations. While advances have been made in the treatment of cancer, many forms/types from a variety of organs remain resistant to current treatment regimens. Thus, novel and safe therapeutic agents or combination of new and currently approved therapeutics are needed to address the growing need in this field.

SUMMARY OF THE INVENTION

In a first aspect, the present invention provides methods for preparing an occidiofungin formulation comprising combining one or more cyclodextrins with occidiofungin. Some embodiments may provide for said one or more cyclodextrins dissolved in an aqueous solvent. Optionally, the methods may further comprise adding one or more additional chemotherapeutic agents to the formulation comprising occidiofungin and the one or more cyclodextrins. Chemotherapeutic agents include those substances inhibiting cell proliferation and/or inducing cell death.

In another aspect, the present invention provides a formulation comprising occidiofungin and one or more cyclodextrins. In some embodiments, the formulation also comprises an aqueous buffer or carrier. The formulation may further comprise one or more chemotherapeutic agents. Various embodiments provide a formulation that can be provided in a unit dosage form or lyophilized.

In still another aspect, the present invention provides for methods of treating proliferative diseases, such as cancer, comprising the administration of a formulation as described herein to a subject in need thereof, such as a subject having a proliferative disease.

BRIEF DESCRIPTION OF THE DRAWINGS

The patent or application file contains at least one drawing executed in color. Copies of this patent or patent application publication, with color drawing(s), will be provided by the Office upon request and payment of the necessary fee. Further advantages of the invention will become apparent by reference to the detailed description of preferred embodiments when considered in conjunction with the drawings which form a portion of the disclosure and wherein:

FIGS. 2A-2L show representative magnifications of histological slides of mice treated with a 5 mg/kg i.v. dose of occidiofungin. (FIG. 2A) Esophagus (200× magnification), (FIG. 2B) Stomach (200× magnification), (FIG. 2C) Small Intestine (200× magnification), (FIG. 2D) Colon (200× magnification), (FIG. 2E) Liver (200× magnification), (FIG. 2F) Pancrease (200× magnification), (FIG. 2G) Spleen (200× magnification), (FIG. 2H) Kidney (200× magnification), (FIG. 2I) Lung (200× magnification), (FIG. 2J) Heart (200× magnification), (FIG. 2K) Brain (100× magnification), and (FIG. 2L) Brain (200× magnification). There were no histological abnormalities in the organ tissues of the treated mice from this experiment.

FIGS. 6A-6B show calibration curves of occidiofungin (A in FIGS. 6A and B in FIG. 6B, respectively) using standard concentrations of occidiofungin in plasma.

FIG. 7A shows occidiofungin (in DPPG vesicles) in collected blood samples as a function of time in a linear scale. FIG. 7B shows the same in log 10 scale.

DETAILED DESCRIPTION

Figure 1:
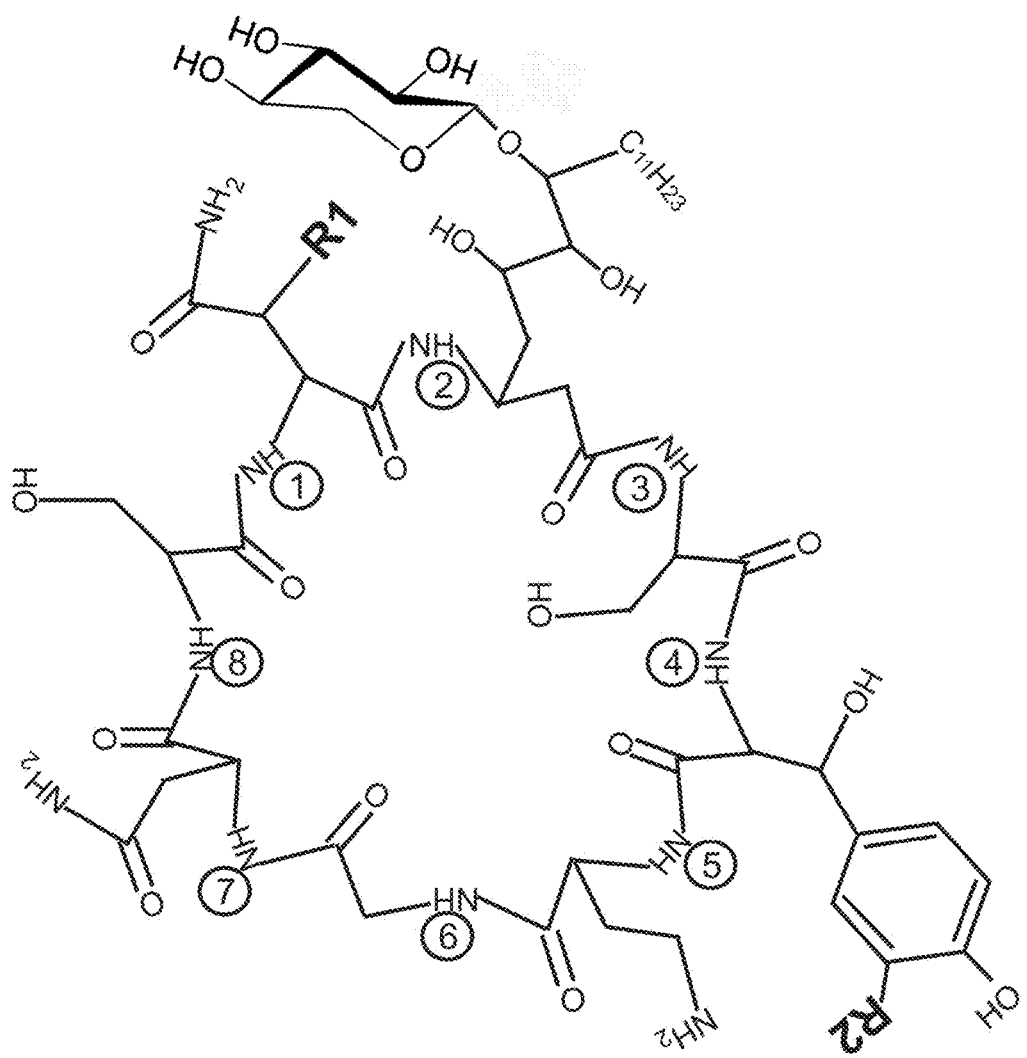
FIG. 1 depicts the covalent structure of occidiofungin. Circles with numbers therein represent amino acid positions: Asn/β-hydroxy Asn1, Novel Amino Acid (NAA2), Ser3, β-hydroxy Tyr/chloro β-hydroxy Tyr4, 2,4-diaminobutyric acid (DABA)5, Gly6, Asn7, and Ser8. R1 and R2 represent natural variations in the covalent structure. R1 is either a proton or hydroxyl group, and R2 is either a proton or chlorine—all of which are referred to herein as occidiofungin.

The following detailed description is presented to enable any person skilled in the art to make and use the invention. For purposes of explanation, specific details are set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

In a first aspect, the present invention provides methods for preparing an occidiofungin formulation comprising combining one or more cyclodextrins with occidiofungin. In some preferred embodiments, the one or more cyclodextrins is/are dissolved in an aqueous solvent. Optionally, the method may comprise further adding one or more additional chemotherapeutic agents to the formulation comprising occidiofungin and the one or more cyclodextrins. In this aspect of the invention, occidiofungin can be present in an amount ranging from 20 μg/mL to 2 mg/mL (or higher, e.g., 1 g/mL). As described below, many factors will be used by a person of skill in the art to determine an appropriate dosage amount. Chemotherapeutic agents, discussed in more detail below, include those substances inhibiting cell proliferation and/or inducing cell death.

In another aspect, the present invention provides a formulation comprising occidiofungin and one or more cyclodextrins. In some preferred embodiments, the formulation also comprises an aqueous buffer or carrier. The formulation may further comprise one or more chemotherapeutic agents. Occidiofungin can be present in an amount ranging from 20 μg/mL to 2 mg/mL (or higher, e.g., 1 g/mL). As described below, many factors will be used by a person of skill in the art to determine an appropriate dosage amount. Various embodiments provide a formulation that can be provided in a unit dosage form or lyophilized.

In still another aspect, the present invention provides for methods of treating proliferative diseases, such as cancer, comprising the administration of a formulation as described herein to a subject in need thereof, such as a subject having a proliferative disease.

Occidiofungin is a cyclic glycopeptide compound effective against a broad range of fungal pathogens of plants and animals. The compound structures are disclosed in United States Patent Application Publication 2011/0136729 A1, which is hereby incorporated by reference in its entirety. United States Patent Application Publication 2014/0147416 A1 (which is hereby incorporated by reference in its entirety) discloses methods of making compositions enriched for particular diasteromers/conformers of occidiofungin and such enriched compositions can also be used to formulate compositions as disclosed herein. Thus, the term occidiofungin, as used herein, includes all forms of occidiofungin (i.e., occidiofungin enriched for a particular natural diasteromer/conformer, including, but not limited to, occidiofungin A and occidiofungin B, and non-enriched occidiofungin). Any desired amount of occidiofungin can be used in the formulation of the compositions disclosed herein (for example, in an amount ranging from 20 μg/mL to 2 mg/mL or higher (e.g., 1 g/mL)). As described below, many factors will be used by a person of skill in the art to determine an appropriate dosage amount.

Occidiofungin salts can be formulated into compositions disclosed herein. Such salts include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate persulfate, 3-phenylpropionate, picrate, pivalate, propionate, succinate, sulfonate, tartrate, thiocyanate, tosylate, and undecanoate. Base salts include alkali metal salts such as potassium and sodium salts, alkaline earth metal salts such as calcium and magnesium salts, and ammonium salts with organic bases such as dicyclohexylamine salts and N-methyl-D-glucamine.

Cyclodextrins are a family of compounds made up of sugar molecules bound together in a ring (cyclic oligosaccharides). In the context of preparing formulations as disclosed herein, any suitable cyclodextrin or combination of cyclodextrins may be used. In one embodiment, the cyclodextrin is selected from the group consisting of β-cyclodextrin (seven sugar ring molecule), α-cyclodextrin (six membered sugar ring molecule), γ-cyclodextrin (eight sugar ring molecule), cyclomaltonose (nine sugar ring molecule), and variants thereof, such as hydroxypropyl-β-cyclodextrin (HP-CD), sulfobutylether-β-cyclodextrin (SBE-CD), hydroxyethyl-β-cyclodextrin (HE-CD), methyl-β-cyclodextrin (M-CD), dimethyl-β-cyclodextrin (DM-CD), randomly dimethylated-β-cyclodextrin (RDM-CD), randomly methylated-β-cyclodextrin (RM-CD), carboxymethyl-β-cyclodextrin (CM-CD), carboxymethyl ethyl-β-cyclodextrin (CME-CD), diethyl-β-cyclodextrin (DE-CD), tri-O-methyl-β-cyclodextrin (TRIMEB), tri-O-ethyl-β-cyclodextrin (TE-CD), tri-O-butyryl-β-cyclodextrin (TB-CD), tri-O-valeryl-β-cyclodextrin (TV-CD), di-O-hexanoyl-β-cyclodextrin (DH-CD), glucosyl-β-cyclodextrin ($G_1$-CD), maltosyl-β-cyclodextrin ($G_2$-CD), and 2-hydroxy-3-trimethyl-ammoniopropyl-β-cyclodextrin (HTMAPCD) (See Reference 27). In preferred embodiments, the cyclodextrin is a variant of a β-cyclodextrin, such as hydroxypropyl-β-cyclodextrin (HP-CD), sulfobutylether-β-cyclodextrin (SBE-CD), and combinations thereof.

Any suitable concentration of cyclodextrin(s) is suitable for the formulation method, the formulations, and the methods of treatment disclosed herein. In preferred embodiments, the suitable concentration of cyclodextrin(s) is any amount that can be dissolved in an aqueous solvent. For example, a preferred aqueous formulation can contain occidiofungin dissolved in an aqueous solution that contains between about 0.5% to about 10% weight/volume (w/v) of one or more cyclodextrins. As a non-limiting example, a 0.5% weight/volume aqueous solution would contain 0.5 gram of cyclodextrin dissolved in a volume of an aqueous solvent sufficient to make 100 mL of solution into which occidiofungin is then formulated. Any suitable aqueous solvent in which cyclodextrins can be dissolved may be used. In various embodiments, the aqueous solvent is water, buffers (e.g., pharmaceutically acceptable buffers and/or excipients) or other aqueous solvents.

Pharmaceutically acceptable buffers and/or excipients can include, Ringer's solution, isotonic saline, isotonic glucose solutions, distilled water, phosphate buffered saline, or other pharmaceutically acceptable buffers and/or excipients known in the art.

Chemotherapeutic agents include those substances inhibiting cell proliferation and/or inducing cell death. In one embodiment a chemotherapeutic agent is selected from the group of gemcitabine, telozolomide, nitrosoureas, vinca alkaloids, antagonists of purine and pyrimidines bases, cytostatic antibiotics, camphotecine derivatives, anti-estrogenes, anti-androgens and analogs of gonadotropin releasing hormone. Other non-limiting examples of chemotherapeutic agents include nitrosoureas such as ACNU, BCNU, CCNU, and/or HCNU. Synonyms for ACNU are 3-[(-4-Amino-2-methyl-5-pyrimidinyl)methyl]-1-(2-chloroethyl)-1-nitrosourea hydrochloride, CS-439 HCl, Nidran hydrochloride, Nimustine Hydrochloride, NSC-245382. BCNU is Bischoroethylnitrosourea, the chemical name is N,N'-bis(2-chlorethyl)-N-nitroso-urea, other names are BiCNU, carmustine. CCNU is 1-(2-Chloroethy)-3-cyclohexyl-1-nitroso-urea. Synonyms are N-(2-chloroethyl)-N-cyclohexyl-N-nitroso-urea, Belustine, Cee NU, Chloroethylcyclohexylnitrosourea, ICIG 1109, Lomustine, NSC 79037. One chemical name for temozolomide is 3,4-dihydro-3-methyl-4-oxoimidazo->5,1d'1,2,3,4-tetrazin-8-carboximide. Other names for temozolomide are Temodal, Temodar, methazolastone, CCRG81045, SCH52365, NSC362856, M&B39836. Synonyms for teniposide are 4'-Demethylepipodophyllotoxin, 9-(4,6-O-2-thenylidene-b-D-glucopyranoside), Epipodophyllotoxin, EPT, Teniposide VM-26, VM 26, 5,8,8a,9-Tetrahydro-5-(4-hydroxy-3,5-dimethoxyphenyl)-9-{[4,6-O-(2-thienylmethylene)-b-D-glucopyranosyl]oxy}furo[3',4':6,7]naphatho[2,3-d]-1,3-dioxol-6(5aH)-one.

In another embodiment the chemotherapeutic agent can be cytotoxic antibiotics, e.g., doxorubicin, pegylated liposomal doxorubicin (CAELYX®), 5-fluorodeoxyuridine, 5-fluorouracil, 5-fluorouridine, gemcitabine, procarbazine, Taxol™, Taxotere™, temozolomide, vinblastine, vincristine, Non-limiting examples of vinca alkaloids comprise vincristine, vinblastine, vindesine and their active derivatives. An antagonist of the purine and pyrimidine bases may be selected from the group of 5-tluorouracile, 5-fluorodeoxiuridine, cytarabine and gemcitabine. In other embodiments the chemotherapeutic agent is selected from the group of doxorubicin and liposomal PEGylated doxorubicin, the camphthotecine delivative is selected from the group of irinotecane and topotecane, the anti-estrogenes are selected from the group of tamoxikn, exemestane, anastrozole and fulvestrant, the anti-androgens are selected from the group of flutamide and bicalutamide, the anti-progesterones are selected from the group of mifepriston, the analogs of gonadotropin releasing honnone are selected from the group of leuprolide and gosereline.

Other non-limiting examples of other chemotherapeutic agents include: acivicin; aclarubicin; acodazole hydrochloride; acromne; adozelesin; Adriamycin™; aldesleukin; altretamine; ambornycin; ametantrone acetate; aminoglutethimide; amsacrine; anastrozole; anthramycin; asparaginase; asperlin; Avastin™; azacitidine; azetepa; azotomycin; hatimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; cetuximab; chlorambucil; cirolemycin; cisplatin; cladribine; crisnatol mesylate; cyclophosphamide; cytarabine; dacarbazine; DACA (N-[2-(dimethyl-amino)ethyl]acridine-4-carboxamide); dactinomycin; daunorubicin hydrochloride; daunomycin; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; erlotinib; esorubicin hydrochloride; estramustine; estramustine phosphate sodium; etanidazole; ethiodized oil $I^{131}$; etoposide; etoposide phosphate; etoprine; fadrozole hydrochloride; fazarahine; fenretinide; floxuridine; fludarabine phosphate; 5-fluorouracil; 5-FdUMP; flurocitahine; fosquidone; fostriecin sodium; gefitinib; gemcitabine; gemcitabine hydrochloride; gold (Au) 198; hydroxyurea; idamhicin hydrochloride; ifosfamide; ilmofosine; imatinih mesylate; interferon alfa-2a; interferon alfa-2b; interferon alfa-nl; interferon alfa-n3; interferon beta-I a; interferon gamma-I b; iproplatin; Iressa™; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindornide; mitocarcin; mitocromin; mitogillin; mitomalcin; mitomycin; mitosper: mitotane; mitoxantrone hydrochloride; mycophenolic acid; nocodazole; nogalamycin; ormaplatin; oxaliplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycm; puromycm hydrochloride; pyrazofurin; riboprine; rituximab; rogletimide; safinol; safingol hydrochloride; semustine; simtrazene; sparfosate sodium; sparsomycm; spirogennanium hydrochloride; spiromustine; spiroplatin; streptonigrin; streptozocin; strontium chloride Sr 89: sulofenur: talisomycin; tamoxifen; taxane; taxoid; tecogalan sodium; tegafur; teloxantrone hydrochloride; temoporfin; teniposide; teroxirone; testolactone; thiamiprine; thioguanine; thiotepa; Thymitaq™; tiazofurin; tirapazamine; Tomudex™; TOP-53; topotecan hydrochloride; toremifene citrate; trastuzumab; trestolone acetate; triciribine phosphate; trimetrexate; trimetrexate glucuronate: triptorelin; tubulozole hydrochloride; uracil mustard; uredepa; vapreotide; verteporfin; vinblastine; vinblastine sulfate; vincristine; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride; 2-chlorodeoxyadenosine; 2'-deoxformycin; 9-aminocamptothecin; raltitrexed; N-propargyl-5,8-dideazafolic acid; 2-chloro-2'-arabino-fluoro-2'-deoxyadenosine; 2-chloro-2'-deoxyadenosine; anisomycin; trichostatinA; hPRL-G 129R; CEP-751; and iinomide. Other chemotherapeutic agents include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; arnbarnustine; amidox; amifostine: aminolevulinic acid; amrubicin; amsacrme; anagrellde; anastrozole; andrographolide; angiogenesis inhibitors; antagonist D; antagonist G; Antarelix™; antidorsalizing morphogenetic protein-1; antiandrogen, prostatic carcmoma; antiestrogen; antineoplaston; antisense oligonucleotides; aphidicobn glycinate; apoptosis gene modulators; apoptosis regulators; apurinic acid; ara-CDP-DL-PTBA); arginine deaminase; asulacrine; atamestane; atrimustine; axinastatin 1; axinastatin 2; axinastatin 3; azasetron; azatoxin; azatyrosine; baccatin III derivatives; balanoL batimastat; BCR/ABL antagonists; benzochlorins; benzoylstaurosporine; beta lactam derivatives; beta-alethine; betaclamycin B; betulinic acid; bFG F inhibitor; bicalutamide; bisantrene; bisaziridinylspermine; bisnafide; bistratene A; bizelesin; breflate; hropirimine; budotitane; huthionine sulfoximine; calcipotriol; calphostin C; camptothecin derivatives (e.g., 10-hydroxy-camptothecin); canarypox IL-2; capecitabine; carboxamide-aminotriazole; carboxyamidotriazole; CaRest M3™; CARN 700; cartilage derived inhibitor; carzelesin; casein kinase inhibitors (lCOS); castano spermine; cecropin 13; cetrorelix; chlorins; chloroquinoxaline sulfonamide; cicaprost; cis-porphyrin; cladribine; clomifcne analogues; clotrimazole; collisrnycin collisrnycin B; combretastatin A4; combretastatin analogue; conagemn; crambescidin 816; crisnatol; cryptophycin 8; cryptophycin A derivatives; curacin A; cyclopentanthraquinones; cycloplatam; cypernycm; cytarabine ocfosfate; cytolytic factor; cytostatln; dacliximab; decitablne; dehydrodidemnin B; deslorelin; dexifosfamide; dexrazoxane; dexverapamil; diaziquone; didemnin B; didox; diethylnorspermine; dihydro-5-azacytidine; 9-dihydrotaxol; dioxamycin; diphenyl spiromustine; discodermolide; docosanol; dolasetron; doxitluridine; droioxlfene; dronabinol; duocarmycin SA; ebseien; ecornustine; edeifosine; edrecolomab; etlomithine; elemene; emitefur; epimbicin; epothilones including desoxyepothilones (A and B); epithilones; epristeride; estramustine analogue; estrogen agonists; estrogen antagonists; etanidazole; etoposide; etoposide 4'-phosphate (Etopofos®); exemestane; fadrozoie; fazarabine; fenretinide; filgrastim; finasteride; flavopiridol; flezeiastine; fluasterone; fludarahine; fluorodaunonmicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; hereglllin; hexamethylene bisacetamide; hypericin; lbandronic acid; idambicin; idoxifene; idramantone; ilmofosine; ilomastat; imidazoacridones; imiquimod; immunostimulant peptides; insulin-like growth factor-I receptor inhibitor; interferon agonists; interferons; interleukins; iobenguane; iododoxorubicin; ipomeanol, 4-; irinotecan; iroplact; irsogladine; isobengazole; isohornohalicondrin B; itasetron; jaspiakinolide; kahalalide F; lamellarin-N triacetate; lanreotlde; leinamycin; lenograstim; lentinan sulfate; leptolstatin; letrozole; leukemia inhibiting factor; leukocyie alpha interferon; leuprolide+estrogen+progesterone; leuprorelin; levamisole; liarozole; linear polyamine analogue; lipophilic disaccharide peptide; lipophilic platinmn compounds; lissoclinamide lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocoi; maspin; matrilysin inhibitors; matrix metalloproteinase inhibitors; menogaril; merbarone; Meterelin™; methioninase; metoclopramide; MIF inhibitor; mifepristone; miltefosine; mirimostim; mismatched double stranded RNA; Mithracin™; mitoguazone; mitolactol; mitomycin analogues; mitonafide; mitotoxin fibroblast growth factor-saporin; mitoxantrone; mofarotene; molgramostim: monoclonal antibody, human chorionic gonadotrophin; monophosphoryl lipid A+myobacterium cell wall SK; mopidamol; multiple drug resistance gene inhibitor; multiple tumor suppressor I-based therapy; mustard anticarcinoma agents; mycaperoxide B; mycobacterial cell wall extract; myriaporone; N-acetyldinaline; N-substituted benzamides; nafarelin; nagrestip; naioxone+pentazocine; napavm; naphterpin; nartograstim; nedaplatin; nemombicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracm; oral cytokine inducer; ormaplatin; osaterone; oxaiiplatin; oxaunomycm; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perilyl alcohol; phenazinomycin: phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; podophyllotoxin; porfimer sodium; porfiromycin; propyl bis-acridone; prostaglandin 12; proteasome inhibitors; protein A-based immune modulator; protein kinase C inhibitor; protein kinase C inhibitors, microalgal; protein tyrosine pbosphatase inhibitors; punne nucleoside phosphorylase inhibitors; purpunns; pyrazoioacridine; pyridoxylated hemoglobin polyoxyethylene conjugate; raf antagonists; raltitrexed; ramosetron; ras famesyl protein transferase inhibitors; ras inhibitors; ras-GAP inhibitor; retellipptine demethylated; rhenium Re 186 etidronate; rhizoxin; ribozymes; RH retinamide; rogletimide; rohitukine; romurtide; roquinimex; rubiginone B 1; ruboxyl; safingoi; saintopin; SarCNU; sarcophytoi A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; soiverol; somatomedin binding protein; sonermin; sparfosic acid; spicamycin D; spiromustine; spienopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swamsomne; synthetic glycosaminoglycans; tallimustine; tamoxifen methiodide; tauromustine; tazarotene; tecogaian sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thyrnaifasin; thymopoietin receptor agonist; thyrnotrinan; thyroid stimulating honnone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system; erythrocyte gene therapy; velaresol; veramine; verdins; verteporfin; vinorelbine; vinxaltine; vitaxin; and/or vorozole.

Another aspect of the invention provides for suitable dosage forms for delivery of the pharmaceutical occidiofungin compositions disclosed herein. In non-limiting embodiments, the dosage form is formulated into a form selected from the group consisting of tablets, gelcaps, softgels, liquid formulations, capsules, troches, lozenges, aqueous or oily suspensions, dispersible powders or granules, emulsion, hard or soft capsules, syrups, or elixirs.

The formulations disclosed herein can be administered orally, topically, parenterally, by inhalation or spray, or rectally in dosage unit formulations containing conventional non-toxic pharmaceutically acceptable carriers, adjuvants, and vehicles. The term parenteral as used herein includes percutaneous, subcutaneous, intravascular (e.g., intravenous), intramuscular, or intrathecal injection or infusion techniques and the like.

In another aspect, the present invention provides methods for treating one or more proliferative disorders, such as cancer, comprising administering to a subject in need thereof a formulation comprising one or more cyclodextrins and occidiofungin in an amount effective to treat the proliferative disorder. In preferred embodiments, the formulation further comprises an aqueous solvent. The subject can be any suitable individual having a proliferative disorder, such as a cancer. For example, the subject can be a mammal (such as a human or a non-human animal such as a rodent, chimpanzee, monkey, or dog). In various embodiments, the method can further comprise the administration of one or more additional chemotherapeutic agents. The additional chemotherapeutic agent(s) is preferably suitable for the treatment of a proliferative disorder (such as a cancer). More preferably, the additional chemotherapeutic agent(s) is suitable for the treatment of the cancer afflicting the subject in need of treatment. In other embodiments, the additional chemotherapeutic agent can be suitable for the treatment of psoriasis (e.g., etanercept, adalimumab, adalimumab, infliximab, golimumab, ustekinumab, soriatane, methotrexate, cyclosporine, or other immunosupressants).

Non-limiting examples of proliferative disorders include pancreatic cancer, bladder cancer, brain tumor, melanoma, renal carcinoma, lung cancer, breast cancer, ovary cancer, prostate cancer, colorectal cancer, gastric cancer, endometrial cancer, osteosarcoma, myosarcoma, blood born tumors, leukemias, tumor metastasis, hemangiomas, acoustic neuromas, neurofibromas, trachomas, pyogenic granulomas, astracytoma, acoustic neuroma, blastoma, Ewing's tumor, craniopharyngloma, ependymoma, medulloblastoma, glioma, hemangloblastoma, Hodgkins-lymphoma, medullablastoma, leukemia, mesothelioma, neuroblastoma, neurofibroma, non-Hodgkins lymphoma, pinealoma, retinoblastoma, sarcoma, seminoma, trachomas, Wilm's tumor, bile duct carcinoma, bladder carcinoma, bronchogenic carcinoma, carcinoma of the kidney, cervical cancer, choriocarcinoma, cystadenocarcinome, embrional carcinoma, epithelial carcinoma, esophageal cancer, cervical carcinoma, colon carcinoma, endometrial cancer, gallbladder cancer, gastric cancer, head cancer, liver carcinoma, lung carcinoma, medullary carcinoma, neck cancer, non-small-cell bronchogenic/lung carcinoma, ovarian cancer, pancreas carcinoma, papillary carcinoma, papillary adenocarcinoma, small intestine carcinoma, rectal cancer, renal cell carcinoma, skin cancer, small-cell bronchogenic/lung carcinoma, squamous cell carcinoma, sebaceous gland carcinoma, testicular carcinoma, and uterine cancer. The brain tumor is in particular an oligodendroglioma, are anaplastic oligoastrozytoma, a glioblastoma, a brain metastasis, a myeloma, a plasmocytoma, a glioma, or an astracytoma. In certain embodiments, the proliferative disorders include, but are not limited to, prostate cancer, pancreatic cancer, breast cancer, lymphomas (e.g., B-cell lymphomas), liver cancer, lung cancer, colon cancer, ovarian cancer, and cervical cancer. Non-limiting examples of B-cell lymphomas that can be treated in accordance with the disclosed invention include: Burkitt lymphoma, chronic lymphocytic leukemia/small lymphocytic lymphoma (CLL/SLL), diffuse large B-cell lymphoma, follicular lymphoma, and mantle cell lymphoma.

As would be recognized, the disclosed cancers can be treated using chemotherapeutic agents typically used for a given form of cancer (e.g., cyclophosphamide, hydroxydaunorubicin, vincristine (oncovin), and prednisone/prednisolone (also referred to as CROP) for the treatment of B-cell lymphomas in combination with the disclosed occidiofungin formulations. The additional chemotherapeutic agent can be combined with the disclosed occidiofungin formulations and administered as a single composition or the additional therapeutic agent can be administered separately from the disclosed occidiofungin formulations (e.g., sequentially or at any time during a given therapeutic regimen that includes the disclosed occidiofungin formulations).

As used herein, "treat" or "treating" (and grammatical variants thereof) means accomplishing one or more of the following: (a) reducing the severity of a proliferative disorder in a subject; (b) limiting or preventing a development or progress of symptoms characteristic of a proliferative disorder being treated in a subject; (c) inhibiting a worsening of symptoms characteristic of a disorder being treated in a subject; (d) limiting or preventing a recurrence of a proliferative disorder in a subject that has previously had the proliferative disorder; (e) limiting or preventing a recurrence of symptoms in a subject that was previously symptomatic for the proliferative disorder; and (f) reversing or alleviating, either partially or completely, the growth of tumors, tumor metastases, or other cancer-causing or neoplastic cells in a subject with a proliferative disorder or suspected of having a proliferative disorder.

An effective amount for these uses is intended to be an amount of a therapeutic agent (e.g., a disclosed formulation herein, a chemotherapeutic agent(s), a combination thereof, and other medicines) administered to a subject that is sufficient to constitute a treatment. A person of skill in the art will understand that an effective amount to be administered has to be determined by standard procedure(s) well known by those of ordinary skill in the art and will depend on many factors including, but not limited to, the nature of the compound (specific activity, etc.), the route of administration, the stage and/or severity of the proliferative disorder, certain physiological data of the subject (including, but not limited to, the age, the weight, size, and general state of health of the subject), and the judgment of the prescribing physician. The appropriate dosage may also vary if it is used alone or in combination with another therapeutic agent.

Following are examples which illustrate procedures for practicing the invention. These examples should not be construed as limiting. All percentages are by weight and all solvent mixture proportions are by volume unless otherwise noted.

Example 1—Occidifungin Toxicity Studies

Methods
Mice.
Female BALB/c mice at age of 6-8 weeks old were used. These mice were purchased from Harlan and allowed to acclimate at least 2 weeks after arrival. They were housed on a 12 hour light-dark cycle in a temperature and humidity controlled animal facility that is accredited by the American Association for Accreditation of Laboratory Animal Care. Animal care and use were in accord with NIH Guidelines and Texas A&M University regulations. Protocols used for the mice models were done in accordance to the methods reported by Luster et al. (See Reference 12).

Single Dose Toxicity Study (See Reference 12).

Occidiofungin was produced as previously described and aliquoted and lyophilized into 100 μg quantities in 1.8 mL centrifuge tubes. Solubility of occidiofungin in aqueous buffers is relatively low. Mice (5 mice per group) were given occidiofungin dissolved in 1.5% hydroxy propyl-beta-cylcodextrin suspended in phosphate buffered saline (PBS). Spectrometric inspection at $O.D._{600}$ following addition of vehicle to the purified dried drug had negligible absorbance difference to vehicle without drug, suggesting that the drug went into solution. For the experiments, occidiofungin was administered by intravenous (i.v.) injection into the tail vein at a single dose at 5 mg/kg of body weight. The excipient control in each experiment matched the vehicle. Body weight and clinical signs (movement, posture, skin lesions, appearance of fur indicating normal grooming, and behaviors) were recorded following administration at one, four, eight, sixteen, and twenty-four hours. Necropsies were performed at 24 hours following administration of occidiofungin.

Measurement of Toxicological Parameters (See Reference 12).

Blood and tissue samples from animals dosed at 5 mg/kg of body weight with occidiofungin in 1.5% hydroxy propyl-beta-cylcodextrin suspended in PBS were taken 24 hours following excipient or drug administration. Mice were anesthetized with isofluorane. Blood was then taken from the retroorbital plexus or heart puncture for serum biochemistry assays (alkaline phosphatase, alanine aminotransferase, aspartate aminotransferase, albumin, and blood urea nitrogen) and hematology (white blood cell count and white blood cell differentiation). Body weight was measured immediately before treatment and 24 hours later before the mice were fully anesthetized and fixed in 10% neutral buffered formalin. Histological examination was performed on a portion of each organ by using routine paraffin embedding technique and staining with hematoxylin and eosin (H & E) (See Reference 14). All the sections were examined under light microscopy for pathological changes by a co-author of this paper, who is a board certified veterinary pathologist.

In Vitro Toxicity Screening.

Cancer cell lines, OVCAR8 (Center for Cancer Research (OVAR.8; Sample ID 25)), SW1088 (ATCC-HTB-12), and Toledo (ATCC CRL-2631), and normal human neonatal dermal fibroblasts cell line (ATCC-PCS-201-010) were passaged and prepped as previously described (See References 15-17). OVCAR8, SW1088, and Toledo2631 are ovarian, brain, and B-cell lymphoma cancer cell lines, respectively. This panel of cell lines was chosen based, in part, on their being from very different cancer types in order to discern whether occidiofungin would have a broad spectrum activity towards cancer cell lines of vastly different parental organ/cell types. OVCAR8 cells are widely used in the field of cancer therapeutic research as a panel representative of ovarian cancer in screening experiments for identifying both ovarian-specific and non-specific (i.e., anti-neoplastic activity on multiple cancer cell types) therapeutic agents (See References 28-30). Similarly, SW1088 cells are widely used in the field of cancer therapeutic research as a panel representative of glioma (the most common brain cancer) in screening experiments for identifying both glioma-specific and non-specific therapeutic agents (See References 31-32). Toledo 2631 cells are derived from lymphoma cells, and are used in the field of cancer therapeutic research for identifying lymphoma-specific and non-specific therapeutic agents (See, e.g., Reference 33). Identified agents having non-specific activity in these cell lines and others have been shown to translate/correlate to in vivo activity (See, e.g., Reference 29). Cell counts per plate were calculated to be approximately 50,000 cells/mL. A 10× stock solution of occidiofungin was prepared at 65 μM concentration in 10% dimethyl sulfoxide (DMSO). Two-fold serial dilutions on a 96 well plate were set up in triplicate with starting concentration of 6.5 μM and a final concentration of 3 nM. Bortezomib was used as a comparator for toxicity against human fibroblast and was serially diluted two-fold starting at a concentration of 5 μM and ending at 2.5 nM. Bortezomib is used clinically against myeloma and lymphoma cancers in patients refractory against other chemotherapeutics (See References 18, 19). Furthermore, bortezomib has shown efficacy against a variety of solid tumors and cancer cell lines, making this an appropriate comparison molecule in the panel of cell lines chosen (See References 34-35). The plates were then incubated at 37° C. in 5% $CO_2$ for 48 hours. After 48 hours, cell viability was monitored using CellTiter-Blue (Promega) cell viability assay by measuring the fluorescence emission of a redox activated dye ($579_{EX}/584_{EM}$) using a POLARstar Omega microplate reader (BMG Labtech).

Pharmacokinetics in Mouse.

Six week old female BALB-C mice were used for this experiment. Occidiofungin, at a concentration of 2.5 mg/kg of body weight, was administered through the tail vein of each mouse. Nine mice were randomly selected for this experiment and were grouped into three groups of three mice each. Blood was drawn at 1, 3, 5, 7, 9, 12, 24 and 48 hours post injection (hpi) from the mice. 15 μl of blood was drawn from the lateral saphenous vein of each mouse for the first three time points. Blood from three mice were pooled together and added to 5 μl of 6.4% citric acid to prevent coagulation. From the fourth time point, blood was drawn from the tail vein of the mice. Blood samples were spun down at 13000 rpm for 10 minutes to separate the plasma. The plasma and the blood pellet obtained were stored separately at −20° C. for analysis. The plasma samples were thawed and the occidiofungin was extracted using a final concentration of 50% methanol. The protein precipitate was spun down at 13000 rpm for 10 minutes and the supernatant was used for analysis. The LC-MS/MS components were carried out at ThermoScientific laboratories. Liquid chromatography was done using Acclaim 120 C18 columns (Length: 150 mm; I.D: 2.1 mm; 5 μm) to purify the occidiofungin in the sample. The occidiofungin was then subjected to MS/MS using the ThermoScientific TSQ Vantage. Fragmentation of the occidiofungin (parent mass 1216 m/z) was carried out and the fragment of 1084 m/z, which corresponds to the occidiofungin molecule without the xylose sugar, was used for quantification of occidiofungin. All data were acquired and analyzed using TraceFinder (v 3.1).

Results

Anatomic and Clinical Pathology.

Results shown in TABLE 1 indicate the change in body weight following a single 5 mg/kg i.v. dose after 24 hours. Excipient treated mice body weight ranged between an 8% to 13% body weight gain after treatment and had a 9.6% average increase in body weight. Occidiofungin treated mice weight ranged between a 0% to a 21% body weight loss after treatment and had an average weight loss of 6.2%.

TABLE 1

Percent body weight change, serum chemistry and hematology following administration of drug and excipient control.

| | Single IV Dose of Occidiofungin | |
|---|---|---|
| | 5 mg/kg | 0 mg/kg |
| *Weight Change % | −6.2 ± 9.9 | +9.6 ± 1.9 |
| Serum Biochemistry | | |
| Albumin (g/dl) | 3.1 ± 0.6 | 3.6 ± 0.2 |
| BUN (mg/dl) | 29.6 ± 5 | 24.5 ± 3.3 |
| ALP (U/l) | 99 ± 34 | 116 ± 17 |
| AST (SGOT) U/l | 765 ± 692 | 165 ± 81 |
| *ALT (SGPT) U/l | 521 ± 652 | 36 ± 10 |
| Hematology | | |
| WBC estimate | 4750 ± 1225 | 5830 ± 1550 |
| *Neutrophils % | 43 ± 14 | 16 ± 5 |
| Lymphocytes % | 54 ± 15 | 83 ± 7 |
| Platelet estimate (xK/ul) | 39 ± 21 | 58 ± 58 |

Animals were sacrificed 24 hours following i.v. administration of occidiofungin.
*Signifies statistically significant differences between treated and control group.

A consistent behavioral response was observed at 1 hour and to a lesser extent at 4 hours post i.v. administration, in which the mice were more lethargic than excipient treated mice and had ruffled fur. They were responsive to touch, but would move slower than excipient treated mice. Treatment did not appear to cause typical rodent behaviors associated with severe pain (e.g., writhing, vocalization, or lack of spontaneous locomotion). No other behavioral signs were observed. Mice behavior appeared to be normal by 8, 16, and 24 hour post injection.

Generally, no macroscopic findings were observed by histological examination. No observable differences were present in the microscopic cell morphology or macroscopic tissue morphology of esophagus, stomach, small intestine, colon, liver, pancreas, spleen, kidneys, lungs, heart and brain (FIGS. 2A-2L). Albumin and blood urea nitrogen (BUN) tests were similar for occidiofungin treated and excipient treated mice (TABLE 1). These blood tests are indicative of normal kidney and to some extent liver function. In addition, alkaline phosphatase (ALP) tests were similar between drug and excipient treated mice (Table 1). These results indicate normal liver and bone cell function. Normally aspartate amino transferase (AST) and alanine aminotransferase (ALT) tests are performed in combination with ALP to assess liver function. Elevated levels of AST and ALT do suggest heart or liver damage, but do not necessarily indicate severe organ damage. Generally a ratio of AST to ALT less than one is indicative of liver damage. The ratio in all treated mice was greater than one, suggesting that the liver is not damaged. AST values ranged from 177 to 1528 (U/l) with a mean value of 765 (U/l) and the ALT values ranged from 144 to 1273 (U/l) with a mean value of 521 (U/l) (Table 1). Given the variability in AST and ALT levels in treated mice, only the ALT levels were statistically significant.

White blood cell (WBC) counts were not statistically different between treated and untreated mice. This suggests that occidiofungin i.v. administration at 5 mg/kg had no cytotoxicological effect on blood cells or bone marrow. The absence of elevated levels further suggests normal spleen function. The percentage of neutrophils was statistically different in drug and excipient treated mice, while the percentages of lymphocytes were not statistically different (TABLE 1). The data does suggest an increase in the ratio of neutrophils to lymphocytes, which is indicative of an innate immune response to the drug. However, additional mice and dosing regimens will need to be done to determine if this is a genuine response. Lastly, there was no statistical difference in platelet counts between drug and excipient treated mice, suggesting that occidiofungin does not affect platelet production by the bone marrow or destroy circulating platelets.

In summary, there was no clear evidence for organ specific histological effects of occidiofungin. There were no apparent undesirable effects observed in the serum clinical chemistry and hematology parameters that would preclude additional animal testing of the compound.

Cytotoxic Activity of Occidiofungin on Human Cell Lines.

Figure 3:
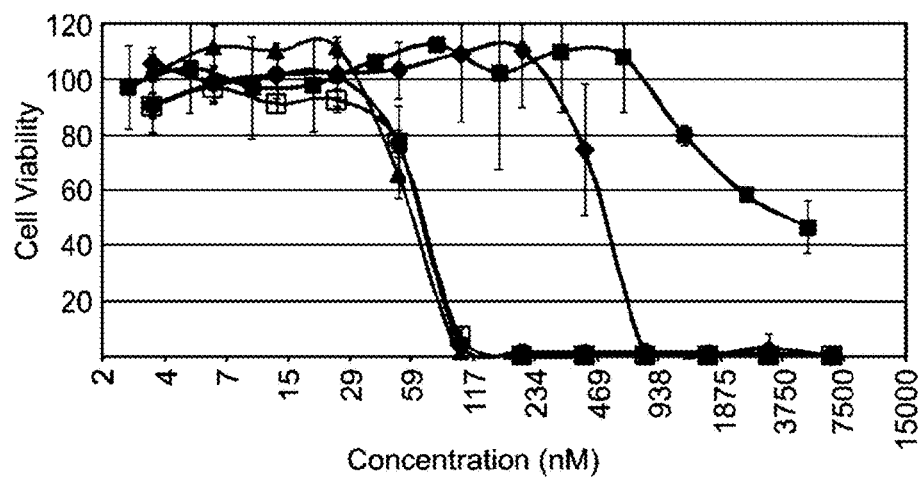
FIG. 3 depicts an in vitro toxicity screen of occidiofungin. Cancer cell lines OVCAR8 (line with triangles), SWI088 (line with circles), and Toledo2631 (lines with open squares) have an average TC50 value of 61 nM, 68 nM, and 70 nM, respectively. In contrast, the average TC50 value of occidiofungin against a human fibroblast cell line (line with filled diamonds) was 533 nM. Bortezomib had a TC50 value of 4,091 nM against the human fibroblast cell line (line with filled squares). Results are mean of three independent experiments with one standard deviation.

Bortezomib is a proteosome inhibitor that has been accepted by the medical community as a potent anticancer drug. It is a potent inhibitor of multiple myeloma and pancreatic tumor growth (See References 18, 19). The proteasome is a multi-catalytic, multi-subunit protease complex that is responsible for the ubiquitin-dependent turnover of cellular proteins (See References 19-21). Interference with the normal function of the proteosome by bortezomib affects cellular pathways that can interfere with transcription, release of cytokines, interfere with DNA repair machinery, and the activation of signalling kinase pathways that alters a cohort of cellular responses (See References 20-23). These activities are exacerbated in multiple cancers. A typical LD50 value for bortezomib is between 20 and 50 nM, while its toxicity is in normal cells with lower metobolism is typically in the micromolar range (See References 20, 24). The activity of bortezomib was compared to the activity of occidiofungin against human fibroblasts. The activity of occidiofungin was approximately eight-fold higher than that of bortezomib against the human fibroblast cell line used in this study (FIG. 3). The TC50 value was 533 nM for occidiofungin, while it was 4,091 nM for bortezomib. The TC50 values for occidiofungin against the ovarian cancer (OVCAR8), astrocytoma brain cancer (SW1088), and B-cell non-hodgkin lymphoma cancer (TOLEDO CRL-2631) cell lines were 61 nM, 68 nM, and 70 nM, respectively. These values are approximately eight-fold higher than that of the normal human primary dermal fibroblasts cell line tested. Furthermore, the activity against the cancer cell lines were ten to twenty-fold higher than what has been reported against *Candida* species.

Pharmacokinetics in Mouse.

Figure 4:
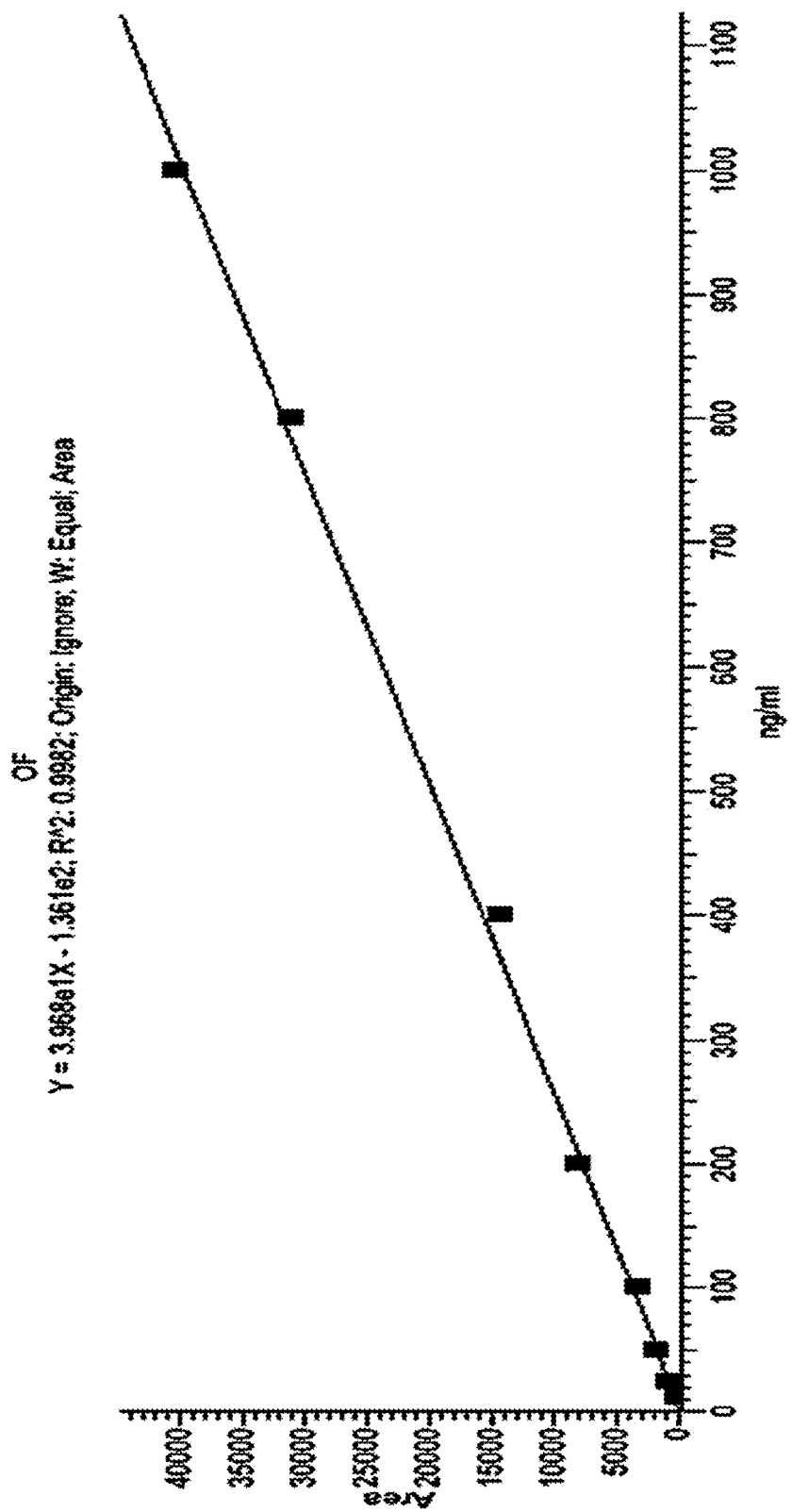
FIG. 4 is a calibration curve of occidiofungin (OF) using known concentrations of occidiofungin in plasma.
Figure 5:
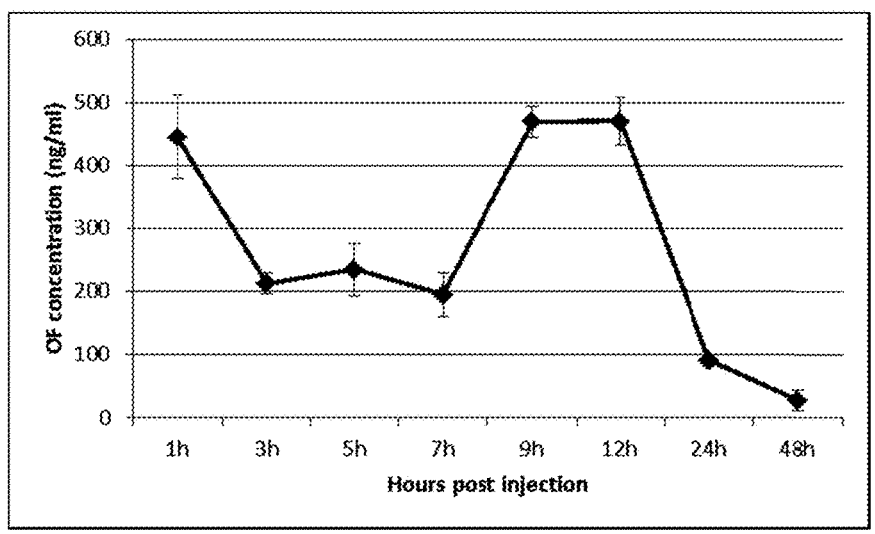
FIG. 5 shows concentration of occidiofungin (OF) versus time following i.v. route of administration. Error bars indicate standard deviation.

A calibration curve was constructed using commercial serum spiked with occidofungin and had an $R^2$ value of 0.9982 (FIG. 4). The calibration was applied to extracted in vivo samples. Based on the sharpness of individual sample curves, the limit of quantification was determined to be 50 ng/ml, although the limit of detection was 12.5 ng/ml. Using this calibration curve, the samples obtained from the mice were plotted. Each data point is done in triplicate and error bars are the standard deviation of the results. Immediately following administration, an increase in blood occidiofungin concentration was seen (FIG. 5). A subsequent drop occurred at three hours post injection (hpi) and occidiofungin concentration peaked around 9 hpi. A peak concentration of 480 ng/ml was observed. The peak concentration was maintained at the same level at 12 hpi. Occidiofungin rapidly cleared from the system by 24 hours and was below the level of quantification by 48 hours. Occidiofungin followed a multi-compartment pharmacokinetic model, in which it appears to be sequestered immediately following injection and released slowly over time. The concentration of occidiofungin is three to six fold higher than the TC50 value observed for the cancer strains tested in the in vitro toxicity assay.

Example 2—Occidifungin Pharmakokinetics Using Vesicles

Methods

Entrapment of occidiofungin in vesicles was done using 1,2-Dioleoyl-sn-glycero-3-phosphocholine (DOPC) and 1,2-dipalmitoyl-sn-glycero-3-[phospho-rac-(3-lysyl(1-glycerol))] (DPPG) from Avanti polar lipids. Lipid cake formation and subsequent hydration was done according to the manufacturer's recommendation. Briefly, 20 mg/ml of DOPC in chloroform was placed in a glass beaker and dried by vacuum evaporation to remove the organic solvent. The lipid film formed was hydrated using a 1 µg/µl solution of occidiofungin in 1.5% (2-Hydroxypropyl)-β-cyclodextrin (Alfa Aesar), while maintaining the lipid concentration at 20 mg/ml and the solution was sonicated to form the vesicles. Similarly, DPPG was mixed with DOPC at a ratio of 9:1 (DOPC:DPPG) to make a homogenous lipid mixture at a concentration of 20 mg/ml and the same process of drying and hydration was repeated to make vesicles. Following vesicle formation, estimation of the amount of occidiofungin trapped inside each type of vesicle was done. The mixture containing free and vesicle trapped occidiofungin was passed through a gel filtration column containing Sephadex G-10 beads. The void volume (containing only the vesicle trapped occidiofungin) was collected and occidiofungin extracted using methanol (50% final concentration). Liquid chromatography was done on the extracted sample, and a standard and the concentration of occidiofungin in the extracted sample was estimated by a comparison of peak volumes.

Occidiofungin in DOPC and DOPC-DPPG, at a concentration of 2.5 mg/kg, with ~1.25 mg/kg entrapped in vesicles, was administered to six female BALB/c mice respectively via intravenous administration. The two kinds of vesicles containing occidiofungin were administered to different groups independently and each experiment had a control group of three mice that received empty vesicles. The mice were weighed prior to the start of the experiment and every 24 hours post injection (hpi).

Figures 7A, 7B:
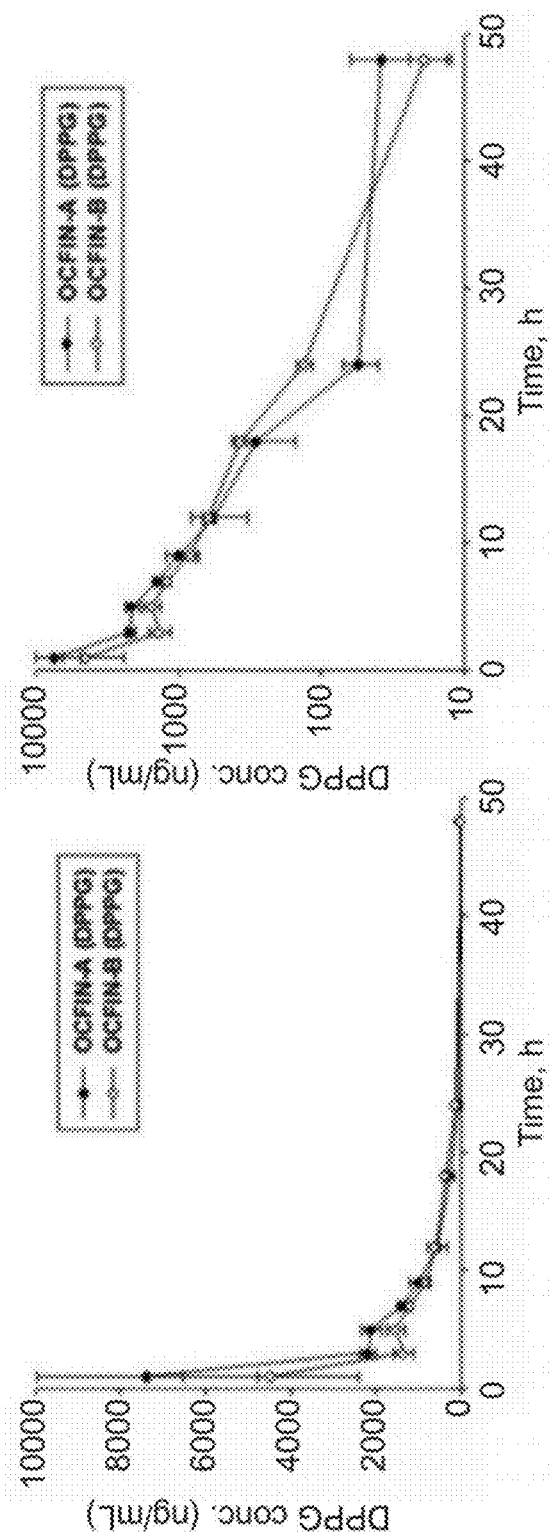
FIGS. 7A-7B show Pharmacokinetics of Occidiofungin packaged in DOPC:DPPG (90:10) vesicles. OCFIN-A: ke1=0.0474 h−1 (r2=0.836) and t½=14.6 h. OCFIN-B: ke1=0.0467 h−1 (r2=0.962) and t½=14.8 h.

Blood was drawn at time points 1 hpi, 3 hpi, 5 hpi, 7 hpi, 9 hpi, 12 hpi, 18 hpi, 24 hpi and 48 hpi. 15 µl of blood was drawn from the lateral saphenous vein of each mouse for the first three time points. Blood from three mice were pooled together and added to 5 µl of 6.4% citric acid to prevent coagulation. From the fourth time point, blood was drawn from the tail vein of the mice. Blood samples were spun down at 13000 rpm for 10 minutes to separate the plasma. The plasma and the blood pellet obtained were stored separately at −20° C. until analysis. The plasma samples were thawed and the occidiofungin was extracted using a final concentration of 50% methanol. The protein precipitate was spun down at 13000 rpm for 10 minutes and the supernatant was used for analysis. Liquid chromatography was done using Acclaim 120 C18 columns (Length: 150 mm; I.D: 2.1 mm; 5 µm) to purify the occidiofungin in the sample. The occidiofungin was then subjected to MS/MS. Fragmentation of the occidiofungin (parent mass 1200 and 1216 Da) was carried out and the fragment of 1068 and 1084 Da m/z, which corresponds to the occidiofungin molecule (A and B forms, respectively) without the xylose sugar, was used for quantification of occidiofungin. A calibration curve constructed using standard concentrations of occidiofungin in plasma was used to analyze the samples obtained from the mice for pharmacokinetics (See FIGS. 6A-6B & 7A-7B). The use of both DOPC or DOPC:DPPG significantly improved the peak plasma concentrations (approximately ten-fold) relative to solubilizing Occidiofungin in β-cyclodextrin alone (Compare FIG. 5 with FIGS. 7A-7B). The higher peak plasma concentration along with a long half-life of Occidiofungin (~14 hours) will promote the therapeutic use of Occidiofungin.

Discussion.

The antifungal activity of occidiofungin against a wide array of fungi has been tested. The antifungal activity was observed at micromolar to sub micromolar concentrations. Initial acute mouse toxicity study was conducted following subcutaneous and intraperitoneal (i.p.) administration (See Reference 11). In this study, we describe a formulation that solubilizes occidiofungin at a concentration that enabled us to evaluate occidiofungin's toxicity following an intravenous route of administration. Furthermore, we evaluated occidiofungin's toxicity against human fibroblast and cancer cells lines. Interestingly, occidiofungin was found to be a potent inhibitor of these cancer cell lines, while there was no significant toxicity observed in mice following a single i.v. dose at 5 mg/kg. This concentration is about seventy-times higher than the concentration that was observed to kill the cancer cells in the in vitro toxicity assay.

Based on the pharmacokinetic data, occidiofungin levels in blood fell shortly after administration. Occidiofungin concentration at 9-12 hpi increased 2.5 times as compared to the concentration at 7 hpi. A peak concentration observed at 9 hours suggests that occidiofungin, upon administration, is getting rapidly sequestered and then released back into the blood stream. Alternatively, occidiofungin could possibly be temporarily modified in the animal system allowing it to escape detection by our mass spectrometry method. Nevertheless, it is observed that occidiofungin is not rapidly cleared out of the system, indicating that the compound is actively available in the blood over a long period of time. The concentration of occidiofungin in blood following a single dose, suggests that it has potential use for the treatment of proliferative diseases, such as cancer. Further studies involving a higher dose of administration and determination of occidiofungin concentration in various tissue samples will be carried out to understand why a drop in the blood occidiofungin concentration is observed.

In our previous mouse toxicity studies, it was clear that higher doses induced more body weight loss, and this change was dose-responsive (See Reference 11). However, body weight loss was not permanent and the mice would regain body weight when dosing ended. Lethargy and ruffled fur were observed in the single i.p. dose experiments on the first and second day after treatment (See Reference 11). The loss in body weight in conjunction with decreased thymus weight and the observed increase in neutrophil percentages suggests that occidiofungin causes a non-specific stress response. Activation of the hypothalamic-pituitary-adrenal axis by a non-specific stress response may increase circulating glucocorticoids that can cause apoptosis in developing thymocytes (See Reference 25). A loss in body weight was also observed following a 5 mg/kg i.v. administration of occidiofungin. In addition, mild lethargy and some ruffled fur were observed following the i.v. administration of occidiofungin. However, these behavioral changes were not as serious as what was observed following i.p. administration (See Reference 11). The mice were responsive and behaved normally by eight hours. There was also an increase in the percentage of neutrophils as observed in the previous study following the i.p. administration of occidiofungin. No other abnormal behavioral signs were observed. Histological examination of treated mice did not exhibit any signs of organ specific toxicity in our prior study following i.p. and subcutaneous administration (See Reference 11), and the mice did not exhibit any signs of organ specific toxicity in the current study following i.v. administration. Even at a relatively high dosage of 5 mg/kg, the lack of organ specific toxicity suggests that this compound may have minimal toxic effects and that the observed weight loss may be mitigated in future efficacy studies.

Viability, terminal deoxynucleotidyl transferase dUTP nick end labeling (TUNEL), reactive oxygen species (ROS) detection, membrane and cell wall stability, and membrane mimetic assays were used in a previous study to characterize the effect of occidiofungin on yeast cells (See Reference 2). Confocal and electron microscopy experiments were used to visualize morphological changes within treated cells. TUNEL and ROS detection assays revealed an increase in fluorescence with increasing concentrations of the antifungal (occidiofungin). Yeast cells appeared to shrink in size and showed the presence of 'dancing bodies' at low drug concentrations (1 μg/ml). Given that occidiofungin's base molecular weight is about 1200 Da, this concentration is around 833 nM. A screen carried out on *Saccharomyces cerevisiae* gene deletion mutants in the apoptotic and autophagy pathways identified the apoptotic gene, Δycal. Deletion of the ycal gene provides a 2-fold increase in resistance. All of the autophagy mutants screened had no difference in sensitivity compared to the wild-type control (See Reference 2). Results from previous experiments demonstrate that yeast cells were dying by an apoptotic mechanism of action. The cellular target of occidiofungin is unknown, but the target is presumably present in mammalian cells given that the cancer cells were sensitive to occidiofungin in the in vitro toxicity assay. Additional studies are needed to determine whether the human cell lines die by apoptosis following exposure to occidiofungin. Furthermore, studies are warranted toward identifying occidiofungin's cellular target given its potential use as a chemotherapeutic.

As used herein, the singular forms "a", "an" and "the" include plural referents unless the context clearly dictates otherwise. "And" as used herein is interchangeably used with "or" unless expressly stated otherwise. Furthermore, all embodiments of any aspect of the invention can be used in combination, unless the context clearly dictates otherwise.

The term "about" is used in this patent application to describe some quantitative aspects of the invention, for example, concentration of cyclodextrin or time of contact. It should be understood that absolute accuracy is not required with respect to those aspects for the invention to operate. When the term "about" is used to describe a quantitative aspect of the invention the relevant aspect may be varied by ±10%. As a non-limiting example, a cyclodextrin solution identified as containing about 0.5% (w/v) cyclodextrin can contain between 0.45 gram and 0.55 gram of cyclodextrin dissolved in an amount of an aqueous solvent sufficient to provide 100 mL of solution.

The terms "comprising," "including," and "having," as used in the claims and specification herein, shall be considered as indicating an open group that may include other elements not specified. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example and not of limitation.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

REFERENCES

1. Ellis, D., Gosai, J., Emrick, C., Heintz, R., Romans, L., Gordon, D., Lu, S., Austin, F., and Smith, L. (2012) Occidiofungin's Chemical Stability and In vitro Potency Against *Candida* species, *Antimicrob Agents Chemother* 56, 765-769.
2. Emrick, D., Ravichandran, A., Gosai, J., Lu, S., Gordon, D. M., and Smith, L. (2013) The antifungal occidiofungin triggers an apoptotic mechanism of cell death in yeast, *Journal Of Natural Products* 76, 829-838.
3. Gu, G., Lu, S., and Wang, N. (2008) AmbR1 and AmbR2 are two transcriptional regulators essential for the antifungal activity of *Burkholderia* sp strain MS14, *Phytopathology* 98, S63-S63.
4. Gu, G., Smith, L., Liu, A., and Lu, S.-E. (2011) A genetic and biochemical map for the biosynthesis of occidiofungin, an antifungal produced by *Burkholderia contaminans* strain MS14, *Applied and Environmental Microbiology* 77, 6189-6198.
5. Gu, G., Wang, N., Chaney, N., Smith, L., and Lu, S.-E. (2009) AmbR1 is a key transcriptional regulator for production of antifungal activity of *Burkholderia contaminans* strain MS14, *FEMS Microbiology Letters* 297, 54-60.
6. Gu, G. Y., Smith, L., Wang, N., Wang, H., and Lu, S. E. (2009) Biosynthesis of an antifungal oligopeptide in *Bur-* kholderia contaminans strain MS14, *Biochemical And Biophysical Research Communications* 380, 328-332.
7. Lu, S.-E., Novak, J., Austin, F. W., Gu, G., Ellis, D., Kirk, M., Wilson-Stanford, S., Tonelli, M., and Smith, L. (2009) Occidiofungin, a unique antifungal glycopeptide produced by a strain of *Burkholderia contaminans*, *Biochemistry* 48, 8312.
8. Ravichandran, A., Gu, G., Escano, J., Lu, S.-E., and Smith, L. (2013) The presence of two cyclase thioesterases expands the conformational freedom of the cyclic Peptide occidiofungin, *Journal Of Natural Products* 76, 150-156.
9. Clancy, C. J., Huang, H., Cheng, S., Derendorf, H., and Nguyen, M. H. (2006) Characterizing the effects of caspofungin on *Candida albicans*, *Candida parapsilosis*, and *Candida glabrata* isolates by simultaneous time-kill and postantifungal-effect experiments, *Antimicrobial Agents And Chemotherapy* 50, 2569-2572.
10. Ernst, E. J., Klepser, M. E., and Pfaller, M. A. (2000) Postantifungal effects of echinocandin, azole, and polyene antifungal agents against *Candida albicans* and *Cryptococcus neoformans*, *Antimicrobial Agents And Chemotherapy* 44, 1108-1111.
11. Wei, T., Cooley, J., Austin, F., Lu, S., Smith, L., and Pruett, S. (2012) Pre-clinical Toxicological Evaluation of Occidiofungin, a Unique Glyco-lipopeptide Antifungal, *International Journal of Toxicology* 31, 326-336.
12. Luster, M. I., Portier, C., Pait, D. G., White, K. L., Jr., Gennings, C., Munson, A. E., and Rosenthal, G. J. (1992) Risk assessment in immunotoxicology. I. Sensitivity and predictability of immune tests, *Fundamental And Applied Toxicology: Official Journal Of The Society Of Toxicology* 18, 200-210.
13. Loftsson, T., and Brewster, M. E. (2012) Cyclodextrins as functional excipients: methods to enhance complexation efficiency, *Journal Of Pharmaceutical Sciences* 101, 3019-3032.
14. Germolec, D. R., Kashon, M., Nyska, A., Kuper, C. F., Portier, C., Kommineni, C., Johnson, K. A., and Luster, M. I. (2004) The accuracy of extended histopathology to detect immunotoxic chemicals, *Toxicological Sciences: An Official Journal Of The Society Of Toxicology* 82, 504-514.
15. Gabay, C., Ben-Bassat, H., Schlesinger, M., and Laskov, R. (1999) Somatic mutations and intraclonal variations in the rearranged Vkappa genes of B-non-Hodgkin's lymphoma cell lines, *European Journal Of Haematology* 63, 180-191.
16. Hamilton, T. C., Young, R. C., and Ozols, R. F. (1984) Experimental model systems of ovarian cancer: applications to the design and evaluation of new treatment approaches, *Seminars In Oncology* 11, 285-298.
17. Wright, W. C., Daniels, W. P., and Fogh, J. (1981) Distinction of seventy-one cultured human tumor cell lines by polymorphic enzyme analysis, *Journal Of The National Cancer Institute* 66, 239-247.
18. Roccaro, A. M., Hideshima, T., Richardson, P. G., Russo, D., Ribatti, D., Vacca, A., Dammacco, F., and Anderson, K. C. (2006) Bortezomib as an antitumor agent, *Current Pharmaceutical Biotechnology* 7, 441-448.
19. Tobinai, K. (2007) Proteasome inhibitor, bortezomib, for myeloma and lymphoma, *International Journal Of Clinical Oncology* 12, 318-326.
20. Cavo, M. (2006) Proteasome inhibitor bortezomib for the treatment of multiple myeloma, *Leukemia* 20, 1341-1352.
21. Chauhan, D., Hideshima, T., Mitsiades, C., Richardson, P., and Anderson, K. C. (2005) Proteasome inhibitor therapy in multiple myeloma, *Molecular Cancer Therapeutics* 4, 686-692.
22. Anderson, K. C. (2004) Bortezomib therapy for myeloma, *Current Hematology Reports* 3, 65-65.
23. Anderson, K. C. (2007) Targeted therapy of multiple myeloma based upon tumor-microenvironmental interactions, *Experimental Hematology* 35, 155-162.
24. Adams, J., Palombella, V. J., Sausville, E. A., Johnson, J., Destree, A., Lazarus, D. D., Maas, J., Pien, C. S., Prakash, S., and Elliott, P. J. (1999) Proteasome inhibitors: a novel class of potent and effective antitumor agents, *Cancer Research* 59, 2615-2622.
25. Fuchs, B. A., and Pruett, S. B. (1993) Morphine induces apoptosis in murine thymocytes in vivo but not in vitro: involvement of both opiate and glucocorticoid receptors, *The Journal Of Pharmacology And Experimental Therapeutics* 266, 417-423.
26. Demain, A. L., and Vaishnav, P. (2011) Natural products for cancer chemotherapy, *Microbial Biotechnology* 4, 687-699.
27. Challa, R., et al. (2005) Cyclodextrins in drug delivery: An updated review, *AAPS PharmSciTech* 6(2), E329-E357.
28. de Moraes, T. A. P., et al. (2014) Synthesis and cytotoxic evaluation of a series of 2-amino-naphthoquinones against human cancer cells, *Molecules* 19(9), 13188-13199.
29. do N Fontes, J. E., et al. (2013) Antitumor effect of the essential oil from leaves of *Guatteria pogonopus* (Annonaceae), *Chemistry & Biodiversity* 10(4), 722-729.
30. Giri, S., et al. (2014) Preclinical therapeutic potential of a nitrosylating agent in the treatment of ovarian cancer. *Plos One* 9(6), e97897-e97897.
31. Jarry, M., et al. (2014) Impact of meriolins, a new class of cyclin-dependent kinase inhibitors, on malignant glioma proliferation and neo-angiogenesis, *Neuro-Oncology* 16(11), 1484-1498.
32. Montgomery, J. P. and P. H. Patterson (2008) Endothelin receptor B antagonists decrease glioma cell viability independently of their cognate receptor, *BMC Cancer* 8, 354-354.
33. Li, W., et al. (2011) Genistein inhibited proliferation and induced apoptosis in acute lymphoblastic leukemia, lymphoma and multiple myeloma cells in vitro, *Leukemia & Lymphoma* 52(12), 2380-2390.
34. Zhang, X., et al. (2014) Inhibition of autophagy enhances apoptosis induced by proteasome inhibitor bortezomib in human glioblastoma U87 and U251 cells, *Mol Cell Biochem* 385, 265-275.
35. Min, H., et al. (2014) Bortezomib induces protective autophagy through AMP-activated protein kinase activation in cultured pancreatic and colorectal cancer cells, *Cancer Chemother Pharmacol* 74(1), 167-76.

We claim:

1. A formulation comprising occidiofungin, and one or more cyclodextrins and an aqueous solvent, wherein either
   a) said occidiofungin is present in an amount ranging from about 20 µg/mL to about 1 g/mL; or
   b) said one or more cyclodextrins comprise between about 0.5% to about 10% weight/volume (w/v) of said formulation.

2. The formulation according to claim 1, wherein said occidiofungin is present in an amount ranging from about 20 µg/mL to about 1 g/mL.

3. The formulation according to claim 1, wherein said one or more cyclodextrins comprise between about 0.5% to about 10% weight/volume (w/v) of said formulation.

4. The formulation according to claim 1, wherein said one or more cyclodextrins is selected from the group consisting of α-cyclodextrin, β-cyclodextrin, γ-cyclodextrin, cyclomaltonose, variants thereof, and any combination thereof.

5. The formulation according to claim 1, wherein said one or more cyclodextrins is selected from the group consisting of hydroxypropyl-β-cyclodextrin, sulfobutylether-β-cyclodextrin, hydroxyethyl β-cyclodextrin, methyl-β-cyclodextrin, dimethyl-β-cyclodextrin, randomly dimethylated-β-cyclodextrin, randomly methylated-β-cyclodextrin, carboxymethyl-β-cyclodextrin, carboxymethyl ethyl-β-cyclodextrin, diethyl-β-cyclodextrin, tri-O-methyl-β-cyclodextrin, tri-O-ethyl-β-cyclodextrin, tri-O-butyryl-β-cyclodextrin, tri-O-valeryl-β-cyclodextrin, di-O-hexanoyl-β-cyclodextrin, glucosyl-β-cyclodextrin, maltosyl-β-cyclodextrin, and 2-hydroxy-3-trimethyl-ammoniopropyl-β-cyclodextrin, or combinations thereof.

6. The formulation according to claim 1, wherein said one or more cyclodextrins is hydroxypropyl-β-cyclodextrin.

7. The formulation according to claim 1, further comprising lipid vesicles.

8. The formulation according to claim 7, wherein said lipid vesicles comprise lipids selected from the group consisting of 1,2-Dioleoyl-sn-glycero-3-phosphocholine, 1,2-dipalmitoyl-sn-glycero-3-[phospho-rac-(3-lysyl(1-glycerol))], and combinations thereof.

9. The formulation according to claim 1, wherein said aqueous solvent is a pharmaceutically acceptable buffer, excipient, or combination thereof.

10. The formulation according to claim 9, wherein said pharmaceutically acceptable buffer, excipient, or combination thereof is selected from the group consisting of Ringer's solution, isotonic saline, isotonic glucose solutions, distilled water, and phosphate buffered saline.

11. The formulation according to claim 1, further comprising at least one chemotherapeutic agent.

12. The formulation according to claim 11, wherein said at least one chemotherapeutic agent is selected from the group consisting of:
analogs of gonadotropin releasing hormone;
nitrosoureas, 1-(4-amino-2-methyl-5-pyrimidinyl) methyl-3-(2-chloroethyl)-3-nitrosourea (ACNU), 1,3-bis (2-chloroethyl)-1-nitroso-urea (BCNU), 1-(2-chloroethyl)-3-cyclohexyl-1-nitrosourea (CCNU), N-hydroxyethylnitroso-N'-chloroethylurea (HCNU);
cytostatic antibiotics, doxorubicin, pegylated liposomal doxorubicin, 5-fluorodeoxyuridine, 5-fluoro-2'-deoxyuridine 5'-monophosphate (5-FdUMP), 5-fluorouracil, 5-fluorouridine, procarbazine, docetaxel, gemcitabine, gemcitabine hydrochloride, telozolomide, epirubicin, epirubicin hydrochloride, idarubicin hydrochloride, zorubicin hydrochloride, aclarubicin, amrubicin, nemorubicin, pirarubicin;
vinca alkaloids, vinblastine, vincristine, vindesine; and
acivicin, acodazole hydrochloride, acronine, ambomycin, ametantrone acetate, aminoglutethimide, anthramycin, asparaginase, asperlin, bevacizumab (Avastin™), azacitidine, azetepa, azotomycin, benzodepa, bisantrene hydrochloride, bisnafide dimesylate, bleomycin sulfate, brequinar sodium, busulfan, cactinomycin, calusterone, caracemide, carbetimer, carboplatin, carmustine, carubicin hydrochloride, cedefingol, cetuximab, chlorambucil, cirolemycin, cisplatin, crisnatol mesylate, cyclophosphamide, cytarabine, dacarbazine, N-[2-(dimethyl-amino)ethyl]acridine-4-carboxamide (DACA), dactinomycin, daunomycin, dexormaplatin, dezaguanine, dezaguanine mesylate, droloxifene citrate, dromostanolone propionate, duazomycin, edatrexate, eflornithine hydrochloride, elsamitrucin, enloplatin, enpromate, epipropidine, erbulozole, erlotinib, esorubicin hydrochloride, estramustine, estramustine phosphate sodium, ethiodized oil I$^{131}$, etoposide phosphate, etoprine, fadrozole hydrochloride, fludarabine phosphate, flurocitabine, fosquidone, fostriecin sodium, gefitinib (Iressa™), gold (Au) 198, hydroxyurea, ifosfamide, imatinib mesylate, interferon alfa-2a, interferon alfa-2b, interferon alfa-n1, interferon alfa-n3, interferon beta-I a, interferon gamma-I b, iproplatin, irinotecan hydrochloride, lanreotide acetate, leuprolide acetate, liarozole hydrochloride, lometrexol sodium, lomustine, losoxantrone hydrochloride, maytansine, mechlorethamine hydrochloride, megestrol acetate, melengestrol acetate, melphalan, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, oxisuran, paclitaxel, peliomycin, pentamustine, peplomycin sulfate, pipobroman, piposulfan, piroxantrone hydrochloride, plicamycin, plomestane, prednimustine, procarbazine hydrochloride, puromycin, puromycin hydrochloride, pyrazofurin, riboprine, rituximab, safinol, safingol hydrochloride, simtrazene, sparfosate sodium, sparsomycin, spirogermanium hydrochloride, spiromustine, spiroplatin, streptonigrin, streptozocin, strontium 89 (Sr) chloride, sulofenur, talisomycin, tamoxifen, taxane, taxoid, teloxantrone hydrochloride, teroxirone, testolactone, thiamiprine, thioguanine, thiotepa, nolatrexed (Thymitaq™), tiazofurin, raltitrexed (Tomudex™), 4beta-aminoalkyl-4'-O-demethyl-4-desoxypodophyllotoxin (TOP-53), topotecan hydrochloride: toremifene citrate, trastuzumab, trestolone acetate, triciribine phosphate, trimetrexate, trimetrexate glucuronate, tubulozole hydrochloride, uracil mustard, uredepa, vinblastine sulfate, vincristine sulfate, vindesine sulfate, vinepidine sulfate, vinglycinate sulfate, vinleurosine sulfate, vinorelbine tartrate, vinrosidine sulfate, vinzolidine sulfate, zeniplatin, zinostatin, 2-chlorodeoxyadenosine, 2'-deoxformycin, 9-aminocamptothecin, raltitrexed, N-propargyl-5,8-dideazafolic acid, 2-chloro-2'-arabino-fluoro-2'-deoxyadenosine, 2-chloro-2'-deoxyadenosine, anisomycin, trichostatin A, hPRL-G129R, CEP-751, linomide, 20-epi-1,25 dihydroxyvitamin D3, 5-ethynyluracil, abiraterone, acylfulvene, adecypenol, adozelesin, aldesleukin, ALL-tyrosine kinase (TK) antagonists, altretamine, ambamustine, amidox, amifostine, aminolevulinic acid, amsacrine, anagrelide, anastrozole, andrographolide, antagonist D, antagonist G, teverelix (Antarelix™), anti-dorsalizing morphogenetic protein-1, antineoplaston, aphidicolin glycinate, apoptosis gene modulators, apoptosis regulators, apurinic acid, 1-beta-D-Arabinofuranosylcytosine 5'-diphosphate-rac-1-S-octadecyl-2-O-palmitoyl-1-thioglycerol (ara-CDP-DL-PTBA), arginine deaminase, asulacrine, atamestane, atrimustine, axinastatin 1, axinastatin 2, axinastatin 3, azasetron, azatoxin, azatyrosine, baccatin III derivatives, balanol, batimastat, breakpoint cluster region/abelson murine leukemia viral oncogene homolog 1 (BCR/ABL) antagonists, benzochlorins, benzoylstaurosporine, beta lactam derivatives, beta-alethine, betaclamycin B, betulinic acid, basic fibroblast growth factor (bFGF) inhibitor, bicalutamide, bisaziridinylspermine, bisnafide, bistratene A, bizelesin, breflate, bropirimine, budotitane, buthionine sulfoximine, calcipotriol, calphostin C, camptothecin derivatives, canarypox IL-2, capecitabine, carboxamide-amino-triazole, carboxyamidotriazole, CaRest M3™, CARN 700, carzelesin, castanospermine, cecropin B, cetrorelix, chlorins, chloroquinoxaline sulfonamide, cicaprost, cis-porphyrin, cladribine, clomifene analogues, clotrimazole, collismycin A, collismycin B, combretastatin A4, combretastatin analogue, conagenin, crambescidin 816, crisnatol, cryptophycin 8, curacin A, cyclopentanthraquinones, cycloplatam, cypemycin, cytarabine ocfosfate, cytolytic factor, cytostatin, dacliximab, decitabine, dehydrodidemnin B, deslorelin, dexifosfamide, dexrazoxane, dexverapamil, diaziquone, didemnin B, didox, diethylnorspermine, dihydro-5-azacytidine, dihydrotaxol, 9-dihydrotaxol, dioxamycin, diphenyl spiromustine, discodermolide, docosanol, dolasetron, doxifluridine, droloxifene, dronabinol, duocarmycin SA, ebselen, ecomustine, edelfosine, edrecolomab, eflornithine, elemene, emitefur, epothilones, desoxyepothilones (A and B), epithilones, epristeride, estramustine analogue, estrogen agonists, estrogen antagonists, androgen antagonists, etanidazole, etoposide, etoposide 4'-phosphate, exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, gelatinase inhibitors, glutathione inhibitors, hepsulfam, heregulin, hexamethylene bisacetamide, hypericin, ibandronic acid, idarubicin, idoxifene, idramantone, ilmofosine, ilomastat, imidazoacridones, imiquimod, immunostimulant peptides, insulin-like growth factor-1 receptor inhibitor, interferon agonists, iobenguane, iododoxorubicin, 4-ipomeanol, irinotecan, iroplact, irsogladine, isobengazole, isohomohalicondrin B, itasetron, jasplakinolide, kahalalide F, lamellarin-N triacetate, lanreotide, leinamycin, lenograstim, lentinan sulfate, leptolstatin, letrozole, leukocyte alpha interferon, leuprolide+estrogen+progesterone, leuprorelin, levamisole, liarozole, lipophilic platinum compounds, lissoclinamide 7, lobaplatin, lombricine, lometrexol, lonidamine, losoxantrone, lovastatin, loxoribine, lurtotecan, lutetium texaphyrin, lysofylline, maitansine, mannostatin A, marimastat, masoprocol, matrilysin inhibitors, matrix metalloproteinase inhibitors, menogaril, merbarone, 2-Me-D-Trp(6),desgly (10)-lhrh ethylamide (Meterelin™), methioninase, metoclopramide, macrophage migration inhibitory factor (MIF) inhibitor, mifepristone, miltefosine, mirimostim, plicamycin (Mithracin™), mitoguazone, mitolactol, mitomycin analogues, mitonafide, mitotoxin fibroblast growth factor-saporin, mitoxantrone, mofarotene, molgramostim, monophosphoryl lipid A+myobacterium cell wall SK, mopidamol, mustard anticarcinoma agents, mycaperoxide B, myriaporone, N-acetyldinaline, N-substituted benzamides, nafarelin, nagrestip, naloxone+pentazocine, napavin, naphterpin, nartograstim, nedaplatin, neridronic acid, nilutamide, nisamycin, nitric oxide modulators, nitroxide antioxidant, nitrullyn, O6-benzylguanine, octreotide, okicenone, onapristone, ondansetron, oracin, ormaplatin, osaterone, oxaliplatin, oxaunomycin, paclitaxel analogues, paclitaxel derivatives, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, perillyl alcohol, phenazinomycin, phenylacetate, picibanil, pilocarpine hydrochloride, piritrexim, placetin A, placetin B, plasminogen activator inhibitor, platinum-triamine complex, podophyllotoxin, porfimer sodium, porfiromycin, propyl bis-acridone, prostaglandin J2, protein A-based immune modulator, protein kinase C inhibitors, microalgal, protein tyrosine phosphatase inhibitors, purine nucleoside phosphorylase inhibitors, purpurins, pyrazoloacridine, pyridoxylated hemoglobin polyoxyethylene conjugate, raf antagonists, ramosetron, ras farnesyl protein transferase inhibitors, ras inhibitors, ras-GAP inhibitor, retelliptine demethylated, rhenium (Re) 186 etidronate, rhizoxin, RII retinamide, rogletimide, rohitukine, romurtide, roquinimex, rubiginone B1, ruboxyl, safingol, saintopin, 2-chloroethyl-3-sarcosinamide-1-nitrosourea (SarCNU), sarcophytol A, sargramostim, Sdi 1 mimetics, semustine, senescence derived inhibitor 1, sizofiran, sobuzoxane, sodium borocaptate, sodium phenylacetate, solverol, sonermin, sparfosic acid, spicamycin D, splenopentin, spongistatin 1, squalamine, stipiamide, stromelysin inhibitors, sulfinosine, superactive vasoactive intestinal peptide antagonist, suradista, suramin, swainsonine, synthetic glycosaminoglycans, tallimustine, tamoxifen methiodide, tauromustine, tazarotene, tecogalan sodium, tegafur, tellurapyrylium, telomerase inhibitors, temoporfin, temozolomide, teniposide, tetrachlorodecaoxide, tetrazomine, thaliblastine, thalidomide, thiocoraline, thrombopoietin, thrombopoietin mimetic, thymalfasin, thymopoietin receptor agonist, thymotrinan, thyroid stimulating hormone, tin ethyl etiopurpurin, tirapazamine, titanocene dichloride, topotecan, topsentin, toremifene, totipotent stem cell factor, tretinoin, triacetyluridine, triciribine, triptorelin, tropisetron, turosteride, tyrphostins, ubiquitin C (UBC) inhibitors, ubenimex, urogenital sinus-derived growth inhibitory factor, urokinase receptor antagonists, vapreotide, variolin B, velaresol, veramine, verdins, verteporfin, vinorelbine, vinxaltine, vitaxin, vorozole, and combinations thereof.

13. The formulation according to claim 11, wherein said at least one chemotherapeutic agent is selected from the group consisting of:
   analogs of gonadotropin releasing hormone;
   nitrosoureas, 1-(4-amino-2-methyl-5-pyrimidinyl) methyl-3-(2-chloroethyl)-3-nitrosourea (ACNU), 1,3-bis (2-chloroethyl)-1-nitroso-urea (BCNU), 1-(2-chloroethyl)-3-cyclohexyl-1-nitrosourea (CCNU), N-hydroxyethylnitroso-N'-chloroethylurea (HCNU);
   cytostatic antibiotics, doxorubicin, pegylated liposomal doxorubicin, 5-fluorodeoxyuridine, 5-fluoro-2'-deoxyuridine 5'-monophosphate (5-FdUMP), 5-fluorouracil, 5-fluorouridine, procarbazine, docetaxel, gemcitabine, gemcitabine hydrochloride, telozolomide;
   vinca alkaloids, vinblastine, vincristine, vindesine; and
   acivicin, acodazole hydrochloride, acronine, ambomycin, ametantrone acetate, aminoglutethimide, anthramycin, asparaginase, asperlin, bevacizumab (Avastin™), azacitidine, azetepa, azotomycin, benzodepa, bisantrene hydrochloride, bisnafide dimesylate, bleomycin sulfate, brequinar sodium, busulfan, cactinomycin, calusterone, caracemide, carbetimer, carboplatin, carmustine, carubicin hydrochloride, cedefingol, cetuximab, chlorambucil, cirolemycin, cisplatin, crisnatol mesylate, cyclophosphamide, cytarabine, dacarbazine, N-[2-(dimethyl-amino)ethyl]acridine-4-carboxamide (DACA), dactinomycin, daunomycin, dexormaplatin, dezaguanine, dezaguanine mesylate, droloxifene citrate, dromostanolone propionate, duazomycin, edatrexate, eflornithine hydrochloride, elsamitrucin, enloplatin, enpromate, epipropidine, epirubicin hydrochloride, erbulozole, erlotinib, esorubicin hydrochloride, estramustine, estramustine phosphate sodium, ethiodized oil $I^{131}$, etoposide phosphate, etoprine, fadrozole hydrochloride, fludarabine phosphate, flurocitabine, fosquidone, fostriecin sodium, gefitinib (Iressa™), gold (Au) 198, hydroxyurea, idarubicin hydrochloride, ifosfamide, imatinib mesylate, interferon alfa-2a, interferon alfa-2b, interferon alfa-n1, interferon alfa-n3, interferon beta-I a, interferon gamma-I b, iproplatin, irinotecan hydrochloride, lanreotide acetate, leuprolide acetate, liarozole hydrochloride, lometrexol sodium, lomustine, losoxantrone hydrochloride, maytansine, mechlorethamine hydrochloride, megestrol acetate, melengestrol acetate, melphalan, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, oxisuran, paclitaxel, peliomycin, pentamustine, peplomycin sulfate, pipobroman, piposulfan, piroxantrone hydrochloride, plicamycin, plomestane, prednimustine, procarbazine hydrochloride, puromycin, puromycin hydrochloride, pyrazofurin, riboprine, rituximab, safinol, safingol hydrochloride, simtrazene, sparfosate sodium, sparsomycin, spirogermanium hydrochloride, spiromustine, spiroplatin, streptonigrin, streptozocin, strontium (Sr) chloride 89, sulofenur, talisomycin, tamoxifen, taxane, taxoid, teloxantrone hydrochloride, teroxirone, testolactone, thiamiprine, thioguanine, thiotepa, nolatrexed (Thymitaq™), tiazofurin, raltitrexed (Tomudex™), 4beta-aminoalkyl-4'-O-demethyl-4-desoxypodophyllotoxin (TOP-53), topotecan hydrochloride: toremifene citrate, trastuzumab, trestolone acetate, triciribine phosphate, trimetrexate, trimetrexate glucuronate, tubulozole hydrochloride, uracil mustard, uredepa, vinblastine sulfate, vincristine sulfate, vindesine sulfate, vinepidine sulfate, vinglycinate sulfate, vinleurosine sulfate, vinorelbine tartrate, vinrosidine sulfate, vinzolidine sulfate, zeniplatin, zinostatin, zorubicin hydrochloride, 2-chlorodeoxyadenosine, 2'-deoxformycin, 9-aminocamptothecin, raltitrexed, N-propargyl-5,8-dideazafolic acid, 2-chloro-2'-arabino-fluoro-2'-deoxyadenosine, 2-chloro-2'-deoxyadenosine, anisomycin, trichostatin A, hPRL-G129R, CEP-751, linomide, 20-epi-1,25 dihydroxyvitamin D3, 5-ethynyluracil, abiraterone, aclarubicin, acylfulvene, adecypenol, adozelesin, aldesleukin, ALL-tyrosine kinase (TK) antagonists, altretamine, ambamustine, amidox, amifostine, aminolevulinic acid, amrubicin, amsacrine, anagrelide, anastrozole, andrographolide, antagonist D, antagonist G, teverelix (Antarelix™), anti-dorsalizing morphogenetic protein-1, antineoplaston, aphidicolin glycinate, apoptosis gene modulators, apoptosis regulators, apurinic acid, 1-beta-D-Arabinofuranosylcytosine 5'-diphosphate-rac-1-S-octadecyl-2-O-palmitoyl-1-thioglycerol (ara-CDP-DL-PTBA), arginine deaminase, asulacrine, atamestane, atrimustine, axinastatin 1, axinastatin 2, axinastatin 3, azasetron, azatoxin, azatyrosine, baccatin III derivatives, balanol, batimastat, breakpoint cluster region/abelson murine leukemia viral oncogene homolog 1 (BCR/ABL) antagonists, benzochlorins, benzoylstaurosporine, beta lactam derivatives, beta-alethine, betaclamycin B, betulinic acid, basic fibroblast growth factor (bFGF) inhibitor, bicalutamide, bisaziridinylspermine, bisnafide, bistratene A, bizelesin, breflate, bropirimine, budotitane, buthionine sulfoximine, calcipotriol, calphostin C, camptothecin derivatives, canarypox IL-2, capecitabine, carboxamide-amino-triazole, carboxyamidotriazole, CaRest M3™, CARN 700, cartilage derived inhibitor, carzelesin, casein kinase inhibitors (ICOS), castanospermine, cecropin B, cetrorelix, chlorins, chloroquinoxaline sulfonamide, cicaprost, cis-porphyrin, cladribine, clomifene analogues, clotrimazole, collismycin A, collismycin B, combretastatin A4, combretastatin analogue, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, deslorelin, dexifosfamide, dexrazoxane, dexverapamil, diaziquone, didemnin B, didox, diethylnorspermine, dihydro-5-azacytidine, dihydrotaxol, 9-dihydrotaxol, dioxamycin, diphenyl spiromustine, discodermolide, docosanol, dolasetron, doxifluridine, droloxifene, dronabinol, duocarmycin SA, ebselen, ecomustine, edelfosine, edrecolomab, eflornithine, elemene, emitefur, epirubicin, epothilones, desoxyepothilones (A and B), epithilones, epristeride, estramustine analogue, estrogen agonists, estrogen antagonists, androgen antagonists, etanidazole, etoposide, etoposide 4'-phosphate, exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, gelatinase inhibitors, glutathione inhibitors, hepsulfam, heregulin, hexamethylene bisacetamide, hypericin, ibandronic acid, idarubicin, idoxifene, idramantone, ilmofosine, ilomastat, imidazoacridones, imiquimod, immunostimulant peptides, insulin-like growth factor-1 receptor inhibitor, interferon agonists, interferons, interleukins, iobenguane, iododoxorubicin, 4-ipomeanol, irinotecan, iroplact, irsogladine, isobengazole, isohomohalicondrin B, itasetron, jasplakinolide, kahalalide F, lamellarin-N triacetate, lanreotide, leinamycin, lenograstim, lentinan sulfate, leptolstatin, letrozole, leukemia inhibiting factor, leukocyte alpha interferon, leuprolide+estrogen+progesterone, leuprorelin, levamisole, liarozole, lipophilic platinum compounds, lissoclinamide 7, lobaplatin, lombricine, lometrexol, lonidamine, losoxantrone, lovastatin, loxoribine, lurtotecan, lutetium texaphyrin, lysofylline, maitansine, mannostatin A, marimastat, masoprocol, matrilysin inhibitors, matrix metalloproteinase inhibitors, menogaril, merbarone, 2-Me-D-Trp(6),desgly(10)-lhrh ethylamide (Meterelin™), methioninase, metoclopramide, macrophage migration inhibitory factor (MIF) inhibitor, mifepristone, miltefosine, mirimostim, plicamycin (Mithracin™), mitoguazone, mitolactol, mitomycin analogues, mitonafide, mitotoxin fibroblast growth factor-saporin, mitoxantrone, mofarotene, molgramostim, monoclonal antibody, human chorionic gonadotrophin, monophosphoryl lipid A+myobacterium cell wall SK, mopidamol, multiple drug resistance gene inhibitor, mustard anticarcinoma agents, mycaperoxide B, mycobacterial cell wall extract, myriaporone, N-acetyldinaline, N-substituted benzamides, nafarelin, nagrestip, naloxone+pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, O6-benzylguanine, octreotide, okicenone, onapristone, ondansetron, oracin, ormaplatin, osaterone, oxaliplatin, oxaunomycin, paclitaxel analogues, paclitaxel derivatives, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, perillyl alcohol, phenazinomycin, phenyl acetate, phosphatase inhibitors, picibanil, pilocarpine hydrochloride, pirarubicin, piritrexim, placetin A, placetin B, plasminogen activator inhibitor, platinum-triamine complex, podophyllotoxin, porfimer sodium, porfiromycin, propyl bis-acridone, prostaglandin J2, proteasome inhibitors, protein A-based immune modulator, protein kinase C inhibitors, microalgal, protein tyrosine phosphatase inhibitors, purine nucleoside phosphorylase inhibitors, purpurins, pyrazoloacridine, pyridoxylated hemoglobin polyoxyethylene conjugate, raf antagonists, ramosetron, ras farnesyl protein transferase inhibitors, ras inhibitors, ras-GAP inhibitor, retelliptine demethylated, rhenium (Re) 186 etidronate, rhizoxin, ribozymes, RH retinamide, rogletimide, rohitukine, romurtide, roquinimex, rubiginone B1, ruboxyl, safingol, saintopin, 2-chloroethyl-3-sarcosinamide-1-nitrosourea (SarCNU), sarcophytol A, sargramostim, Sdi 1 mimetics, semustine, senescence derived inhibitor 1, single chain antigen binding protein, sizofiran, sobuzoxane, sodium borocaptate, sodium phenylacetate, solverol, somatomedin binding protein, sonermin, sparfosic acid, spicamycin D, splenopentin, spongistatin 1, squalamine, stipiamide, stromelysin inhibitors, sulfinosine, superactive vasoactive intestinal peptide antagonist, suradista, suramin, swainsonine, synthetic glycosaminoglycans, tallimustine, tamoxifen methiodide, tauromustine, tazarotene, tecogalan sodium, tegafur, tellurapyrylium, telomerase inhibitors, temoporfin, temozolomide, teniposide, tetrachlorodecaoxide, tetrazomine, thaliblastine, thalidomide, thiocoraline, thrombopoietin, thrombopoietin mimetic, thymalfasin, thymopoietin receptor agonist, thymotrinan, thyroid stimulating hormone, tin ethyl etiopurpurin, tirapazamine, titanocene dichloride, topotecan, topsentin, toremifene, totipotent stem cell factor, tretinoin, triacetyluridine, triciribine, triptorelin, tropisetron, turosteride, tyrosine kinase inhibitors, tyrphostins, ubiquitin C (UBC) inhibitors, ubenimex, urogenital sinus-derived growth inhibitory factor, urokinase receptor antagonists, vapreotide, variolin B, velaresol, veramine, verdins, verteporfin, vinorelbine, vinxaltine, vitaxin, vorozole, and combinations thereof.

14. A method of formulating an occidiofungin formulation comprising combining occidiofungin with one or more cyclodextrins and an aqueous solvent, wherein said occidiofungin formulation comprises either
   a) said occidiofungin in an amount ranging from about 20 μg/mL to about 1 g/mL; or
   b) said one or more cyclodextrins at between about 0.5% to about 10% weight/volume (w/v) of said formulation.

15. The method according to claim 14, wherein said occidiofungin formulation comprises between about 0.5% to about 10% weight/volume (w/v) of said one or more cyclodextrins.

16. The method according to claim 14, wherein said occidiofungin formulation comprises said occidiofungin is present in an amount ranging from about 20 μg/mL to about 1 g/mL.

17. The method according to claim 14, wherein said one or more cyclodextrin is selected from the group consisting of α-cyclodextrin, β-cyclodextrin, γ-cyclodextrin, cyclomaltonose, variants thereof, and any combination thereof.

18. The method according to claim 14, wherein said one or more cyclodextrin is selected from the group consisting of hydroxypropyl-β-cyclodextrin, sulfobutylether-β-cyclodextrin, hydroxyethyl β-cyclodextrin, methyl-β-cyclodextrin, dimethyl-β-cyclodextrin, randomly dimethylated-β-cyclodextrin, randomly methylated-β-cyclodextrin, carboxymethyl-β-cyclodextrin, carboxymethyl ethyl-β-cyclodextrin, diethyl-β-cyclodextrin, tri-O-methyl-β-cyclodextrin, tri-O-ethyl-3-cyclodextrin, tri-O-butyryl-3-cyclodextrin, tri-O-valeryl-3-cyclodextrin, di-O-hexanoyl-β-cyclodextrin, glucosyl-β-cyclodextrin, maltosyl-β-cyclodextrin, and 2-hydroxy-3-trimethyl-ammoniopropyl-β-cyclodextrin, or combinations thereof.

19. The method according to claim 14, wherein said one or more cyclodextrin is hydroxypropyl-β-cyclodextrin.

20. The method according to claim 14, further comprising combining lipid vesicles with said occidiofungin formulation.

21. The method according to claim 20, wherein said lipid vesicles comprise lipids selected from the group consisting of 1,2-Dioleoyl-sn-glycero-3-phosphocholine, 1,2-dipalmitoyl-sn-glycero-3-[phospho-rac-(3-lysyl(1-glycerol))], and combinations thereof.

22. The method according to claim 14, wherein said aqueous solvent is a pharmaceutically acceptable buffer, excipient, or combination thereof.

23. The method according to claim 22, wherein said pharmaceutically acceptable buffer, excipient, or combination thereof is selected from the group consisting of Ringer's solution, isotonic saline, isotonic glucose solutions, distilled water, and phosphate buffered saline.

24. The method according to claim 14, further comprising adding one or more chemotherapeutic agents to said occidiofungin formulation.

25. The method according to claim 24, wherein said one or more chemotherapeutic agents are selected from the group consisting of:
   analogs of gonadotropin releasing hormone;
   nitrosoureas, 1-(4-amino-2-methyl-5-pyrimidinyl) methyl-3-(2-chloroethyl)-3-nitrosourea (ACNU), 1,3-bis (2-chloroethyl)-1-nitroso-urea (BCNU), 1-(2-chloroethyl)-3-cyclohexyl-1-nitrosourea (CCNU), N-hydroxyethylnitroso-N'-chloroethylurea (HCNU);
   cytostatic antibiotics, doxorubicin, pegylated liposomal doxorubicin, 5-fluorodeoxyuridine, 5-fluoro-2'-deoxyuridine 5'-monophosphate (5-FdUMP), 5-fluorouracil, 5-fluorouridine, procarbazine, docetaxel, gemcitabine, gemcitabine hydrochloride, telozolomide, epirubicin, epirubicin hydrochloride, idarubicin hydrochloride, zorubicin hydrochloride, aclarubicin, amrubicin, nemorubicin, pirarubicin;
   vinca alkaloids, vinblastine, vincristine, vindesine; and
   acivicin, acodazole hydrochloride, acronine, ambomycin, ametantrone acetate, aminoglutethimide, anthramycin, asparaginase, asperlin, bevacizumab (Avastin™), azacitidine, azetepa, azotomycin, benzodepa, bisantrene hydrochloride, bisnafide dimesylate, bleomycin sulfate, brequinar sodium, busulfan, cactinomycin, calusterone, caracemide, carbetimer, carboplatin, carmustine, carubicin hydrochloride, cedefingol, cetuximab, chlorambucil, cirolemycin, cisplatin, crisnatol mesylate, cyclophosphamide, cytarabine, dacarbazine, N-[2-(dimethyl-amino)ethyl]acridine-4-carboxamide (DACA), dactinomycin, daunomycin, dexormaplatin, dezaguanine, dezaguanine mesylate, droloxifene citrate, dromostanolone propionate, duazomycin, edatrexate, eflornithine hydrochloride, elsamitrucin, enloplatin, enpromate, epipropidine, erbulozole, erlotinib, esorubicin hydrochloride, estramustine, estramustine phosphate sodium, ethiodized oil I$^{131}$, etoposide phosphate, etoprine, fadrozole hydrochloride, fludarabine phosphate, flurocitabine, fosquidone, fostriecin sodium, gefitinib (Iressa™), gold (Au) 198, hydroxyurea, ifosfamide, imatinib mesylate, interferon alfa-2a, interferon alfa-2b, interferon alfa-n1, interferon alfa-n3, interferon beta-I a, interferon gamma-I b, iproplatin, irinotecan hydrochloride, lanreotide acetate, leuprolide acetate, liarozole hydrochloride, lometrexol sodium, lomustine, losoxantrone hydrochloride, maytansine, mechlorethamine hydrochloride, megestrol acetate, melengestrol acetate, melphalan, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, oxisuran, paclitaxel, peliomycin, pentamustine, peplomycin sulfate, pipobroman, piposulfan, piroxantrone hydrochloride, plicamycin, plomestane, prednimustine, procarbazine hydrochloride, puromycin, puromycin hydrochloride, pyrazofurin, riboprine, rituximab, safinol, safingol hydrochloride, simtrazene, sparfosate sodium, sparsomycin, spirogermanium hydrochloride, spiromustine, spiroplatin, streptonigrin, streptozocin, strontium 89 (Sr) chloride, sulofenur, talisomycin, tamoxifen, taxane, taxoid, teloxantrone hydrochloride, teroxirone, testolactone, thiamiprine, thioguanine, thiotepa, nolatrexed (Thymitaq™), tiazofurin, raltitrexed (Tomudex™), 4beta-aminoalkyl-4'-O-demethyl-4-desoxypodophyllotoxin (TOP-53), topotecan hydrochloride: toremifene citrate, trastuzumab, trestolone acetate, triciribine phosphate, trimetrexate, trimetrexate glucuronate, tubulozole hydrochloride, uracil mustard, uredepa, vinblastine sulfate, vincristine sulfate, vindesine sulfate, vinepidine sulfate, vinglycinate sulfate, vinleurosine sulfate, vinorelbine tartrate, vinrosidine sulfate, vinzolidine sulfate, zeniplatin, zinostatin, 2-chlorodeoxyadenosine, 2'-deoxformycin, 9-aminocamptothecin, raltitrexed, N-propargyl-5,8-dideazafolic acid, 2-chloro-2'-arabino-fluoro-2'-deoxyadenosine, 2-chloro-2'-deoxyadenosine, anisomycin, trichostatin A, hPRL-G129R, CEP-751, linomide, 20-epi-1,25 dihydroxyvitamin D3, 5-ethynyluracil, abiraterone, acylfulvene, adecypenol, adozelesin, aldesleukin, ALL-tyrosine kinase (TK) antagonists, altretamine, ambamustine, amidox, amifostine, aminolevulinic acid, amsacrine, anagrelide, anastrozole, andrographolide, antagonist D, antagonist G, teverelix (Antarelix™), anti-dorsalizing morphogenetic protein-1, antineoplaston, aphidicolin glycinate, apoptosis gene modulators, apoptosis regulators, apurinic acid, 1-beta-D-Arabinofuranosylcytosine 5'-diphosphate-rac-1-S-octadecyl-2-O-palmitoyl-1-thioglycerol (ara-CDP-DL-PTBA), arginine deaminase, asulacrine, atamestane, atrimustine, axinastatin 1, axinastatin 2, axinastatin 3, azasetron, azatoxin, azatyrosine, baccatin III derivatives, balanol, batimastat, breakpoint cluster region/abelson murine leukemia viral oncogene homolog 1 (BCR/ABL) antagonists, benzochlorins, benzoylstaurosporine, beta lactam derivatives, beta-alethine, betaclamycin B, betulinic acid, basic fibroblast growth factor (bFGF) inhibitor, bicalutamide, bisaziridinylspermine, bisnafide, bistratene A, bizelesin, breflate, bropirimine, budotitane, buthionine sulfoximine, calcipotriol, calphostin C, camptothecin derivatives, canarypox IL-2, capecitabine, carboxamide-amino-triazole, carboxyamidotriazole, CaRest M3™, CARN 700, carzelesin, castanospermine, cecropin B, cetrorelix, chlorins, chloroquinoxaline sulfonamide, cicaprost, cis-porphyrin, cladribine, clomifene analogues, clotrimazole, collismycin A, collismycin B, combretastatin A4, combretastatin analogue, conagenin, crambescidin 816, crisnatol, cryptophycin 8, curacin A, cyclopentanthraquinones, cycloplatam, cypemycin, cytarabine ocfosfate, cytolytic factor, cytostatin, dacliximab, decitabine, dehydrodidemnin B, deslorelin, dexifosfamide, dexrazoxane, dexverapamil, diaziquone, didemnin B, didox, diethylnorspermine, dihydro-5-azacytidine, dihydrotaxol, 9-dihydrotaxol, dioxamycin, diphenyl spiromustine, discodermolide, docosanol, dolasetron, doxifluridine, droloxifene, dronabinol, duocarmycin SA, ebselen, ecomustine, edelfosine, edrecolomab, eflornithine, elemene, emitefur, epothilones, desoxyepothilones (A and B), epithilones, epristeride, estramustine analogue, estrogen agonists, estrogen antagonists, androgen antagonists, etanidazole, etoposide, etoposide 4'-phosphate, exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, gelatinase inhibitors, glutathione inhibitors, hepsulfam, heregulin, hexamethylene bisacetamide, hypericin, ibandronic acid, idarubicin, idoxifene, idramantone, ilmofosine, ilomastat, imidazoacridones, imiquimod, immunostimulant peptides, insulin-like growth factor-1 receptor inhibitor, interferon agonists, iobenguane, iododoxorubicin, 4-ipomeanol, irinotecan, iroplact, irsogladine, isobengazole, isohomohalicondrin B, itasetron, jasplakinolide, kahalalide F, lamellarin-N triacetate, lanreotide, leinamycin, lenograstim, lentinan sulfate, leptolstatin, letrozole, leukocyte alpha interferon, leuprolide+estrogen+progesterone, leuprorelin, levamisole, liarozole, lipophilic platinum compounds, lissoclinamide 7, lobaplatin, lombricine, lometrexol, lonidamine, losoxantrone, lovastatin, loxoribine, lurtotecan, lutetium texaphyrin, lysofylline, maitansine, mannostatin A, marimastat, masoprocol, matrilysin inhibitors, matrix metalloproteinase inhibitors, menogaril, merbarone, 2-Me-D-Trp(6),desgly (10)-lhrh ethylamide (Meterelin™), methioninase, metoclopramide, macrophage migration inhibitory factor (MIF) inhibitor, mifepristone, miltefosine, mirimostim, plicamycin (Mithracin™), mitoguazone, mitolactol, mitomycin analogues, mitonafide, mitotoxin fibroblast growth factor-saporin, mitoxantrone, mofarotene, molgramostim, monophosphoryl lipid A+myobacterium cell wall SK, mopidamol, mustard anticarcinoma agents, mycaperoxide B, myriaporone, N-acetyldinaline, N-substituted benzamides, nafarelin, nagrestip, naloxone+pentazocine, napavin, naphterpin, nartograstim, nedaplatin, neridronic acid, nilutamide, nisamycin, nitric oxide modulators, nitroxide antioxidant, nitrullyn, O6-benzylguanine, octreotide, okicenone, onapristone, ondansetron, oracin, ormaplatin, osaterone, oxaliplatin, oxaunomycin, paclitaxel analogues, paclitaxel derivatives, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, perillyl alcohol, phenazinomycin, phenylacetate, picibanil, pilocarpine hydrochloride, piritrexim, placetin A, placetin B, plasminogen activator inhibitor, platinum-triamine complex, podophyllotoxin, porfimer sodium, porfiromycin, propyl bis-acridone, prostaglandin J2, protein A-based immune modulator, protein kinase C inhibitors, microalgal, protein tyrosine phosphatase inhibitors, purine nucleoside phosphorylase inhibitors, purpurins, pyrazoloacridine, pyridoxylated hemoglobin polyoxyethylene conjugate, raf antagonists, ramosetron, ras farnesyl protein transferase inhibitors, ras inhibitors, ras-GAP inhibitor, retelliptine demethylated, rhenium (Re) 186 etidronate, rhizoxin, RII retinamide, rogletimide, rohitukine, romurtide, roquinimex, rubiginone B1, ruboxyl, safingol, saintopin, 2-chloroethyl-3-sarcosinamide-1-nitrosourea (SarCNU), sarcophytol A, sargramostim, Sdi 1 mimetics, semustine, senescence derived inhibitor 1, sizofiran, sobuzoxane, sodium borocaptate, sodium phenylacetate, solverol, sonermin, sparfosic acid, spicamycin D, splenopentin, spongistatin 1, squalamine, stipiamide, stromelysin inhibitors, sulfinosine, superactive vasoactive intestinal peptide antagonist, suradista, suramin, swainsonine, synthetic glycosaminoglycans, tallimustine, tamoxifen methiodide, tauromustine, tazarotene, tecogalan sodium, tegafur, tellurapyrylium, telomerase inhibitors, temoporfin, temozolomide, teniposide, tetrachlorodecaoxide, tetrazomine, thaliblastine, thalidomide, thiocoraline, thrombopoietin, thrombopoietin mimetic, thymalfasin, thymopoietin receptor agonist, thymotrinan, thyroid stimulating hormone, tin ethyl etiopurpurin, tirapazamine, titanocene dichloride, topotecan, topsentin, toremifene, totipotent stem cell factor, tretinoin, triacetyluridine, triciribine, triptorelin, tropisetron, turosteride, tyrphostins, ubiquitin C (UBC) inhibitors, ubenimex, urogenital sinus-derived growth inhibitory factor, urokinase receptor antagonists, vapreotide, variolin B, velaresol, veramine, verdins, verteporfin, vinorelbine, vinxaltine, vitaxin, vorozole, and combinations thereof.

26. The method according to claim 24, wherein said one or more chemotherapeutic agents are selected from the group consisting of:
analogs of gonadotropin releasing hormone;
nitrosoureas, 1-(4-amino-2-methyl-5-pyrimidinyl) methyl-3-(2-chloroethyl)-3-nitrosourea (ACNU), 1,3-bis (2-chloroethyl)-1-nitroso-urea (BCNU), 1-(2-chloroethyl)-3-cyclohexyl-1-nitrosourea (CCNU), N-hydroxyethylnitroso-N'-chloroethylurea (HCNU);
cytostatic antibiotics, doxorubicin, pegylated liposomal doxorubicin, 5-fluorodeoxyuridine, 5-fluoro-2'-deoxyuridine 5'-monophosphate (5-FdUMP), 5-fluorouracil, 5-fluorouridine, procarbazine, docetaxel, gemcitabine, gemcitabine hydrochloride, telozolomide;
vinca alkaloids, vinblastine, vincristine, vindesine; and
acivicin, acodazole hydrochloride, acronine, ambomycin, ametantrone acetate, aminoglutethimide, anthramycin, asparaginase, asperlin, bevacizumab (Avastin™), azacitidine, azetepa, azotomycin, benzodepa, bisantrene hydrochloride, bisnafide dimesylate, bleomycin sulfate, brequinar sodium, busulfan, cactinomycin, calusterone, caracemide, carbetimer, carboplatin, carmustine, carubicin hydrochloride, cedefingol, cetuximab, chlorambucil, cirolemycin, cisplatin, crisnatol mesylate, cyclophosphamide, cytarabine, dacarbazine, N-[2-(dimethyl-amino)ethyl]acridine-4-carboxamide (DACA), dactinomycin, daunomycin, dexormaplatin, dezaguanine, dezaguanine mesylate, droloxifene citrate, dromostanolone propionate, duazomycin, edatrexate, eflornithine hydrochloride, elsamitrucin, enloplatin, enpromate, epipropidine, epirubicin hydrochloride, erbulozole, erlotinib, esorubicin hydrochloride, estramustine, estramustine phosphate sodium, ethiodized oil $I^{131}$, etoposide phosphate, etoprine, fadrozole hydrochloride, fludarabine phosphate, flurocitabine, fosquidone, fostriecin sodium, gefitinib (Iressa™), gold (Au) 198, hydroxyurea, idarubicin hydrochloride, ifosfamide, imatinib mesylate, interferon alfa-2a, interferon alfa-2b, interferon alfa-n1, interferon alfa-n3, interferon beta-I a, interferon gamma-I b, iproplatin, irinotecan hydrochloride, lanreotide acetate, leuprolide acetate, liarozole hydrochloride, lometrexol sodium, lomustine, losoxantrone hydrochloride, maytansine, mechlorethamine hydrochloride, megestrol acetate, melengestrol acetate, melphalan, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, oxisuran, paclitaxel, peliomycin, pentamustine, peplomycin sulfate, pipobroman, piposulfan, piroxantrone hydrochloride, plicamycin, plomestane, prednimustine, procarbazine hydrochloride, puromycin, puromycin hydrochloride, pyrazofurin, riboprine, rituximab, safinol, safingol hydrochloride, simtrazene, sparfosate sodium, sparsomycin, spirogermanium hydrochloride, spiromustine, spiroplatin, streptonigrin, streptozocin, strontium (Sr) chloride 89, sulofenur, talisomycin, tamoxifen, taxane, taxoid, teloxantrone hydrochloride, teroxirone, testolactone, thiamiprine, thioguanine, thiotepa, nolatrexed (Thymitaq™), tiazofurin, raltitrexed (Tomudex™), 4beta-aminoalkyl-4'-O-demethyl-4-desoxypodophyllotoxin (TOP-53), topotecan hydrochloride: toremifene citrate, trastuzumab, trestolone acetate, triciribine phosphate, trimetrexate, trimetrexate glucuronate, tubulozole hydrochloride, uracil mustard, uredepa, vinblastine sulfate, vincristine sulfate, vindesine sulfate, vinepidine sulfate, vinglycinate sulfate, vinleurosine sulfate, vinorelbine tartrate, vinrosidine sulfate, vinzolidine sulfate, zeniplatin, zinostatin, zorubicin hydrochloride, 2-chlorodeoxyadenosine, 2'-deoxformycin, 9-aminocamptothecin, raltitrexed, N-propargyl-5,8-dideazafolic acid, 2-chloro-2'-arabino-fluoro-2'-deoxyadenosine, 2-chloro-2'-deoxyadenosine, anisomycin, trichostatin A, hPRL-G129R, CEP-751, linomide, 20-epi-1,25 dihydroxyvitamin D3, 5-ethynyluracil, abiraterone, aclarubicin, acylfulvene, adecypenol, adozelesin, aldesleukin, ALL-tyrosine kinase (TK) antagonists, altretamine, ambamustine, amidox, amifostine, aminolevulinic acid, amrubicin, amsacrine, anagrelide, anastrozole, andrographolide, antagonist D, antagonist G, teverelix (Antarelix™), anti-dorsalizing morphogenetic protein-1, antineoplaston, aphidicolin glycinate, apoptosis gene modulators, apoptosis regulators, apurinic acid, 1-beta-D-Arabinofuranosylcytosine 5'-diphosphate-rac-1-S-octadecyl-2-O-palmitoyl-1-thioglycerol (ara-CDP-DL-PTBA), arginine deaminase, asulacrine, atamestane, atrimustine, axinastatin 1, axinastatin 2, axinastatin 3, azasetron, azatoxin, azatyrosine, baccatin III derivatives, balanol, batimastat, breakpoint cluster region/abelson murine leukemia viral oncogene homolog 1 (BCR/ABL) antagonists, benzochlorins, benzoyl staurosporine, beta lactam derivatives, beta-alethine, betaclamycin B, betulinic acid, basic fibroblast growth factor (bFGF) inhibitor, bicalutamide, bisaziridinylspermine, bisnafide, bistratene A, bizelesin, breflate, bropirimine, budotitane, buthionine sulfoximine, calcipotriol, calphostin C, camptothecin derivatives, canarypox IL-2, capecitabine, carboxamide-amino-triazole, carboxyamidotriazole, CaRest M3™, CARN 700, cartilage derived inhibitor, carzelesin, casein kinase inhibitors (ICOS), castanospermine, cecropin B, cetrorelix, chlorins, chloroquinoxaline sulfonamide, cicaprost, cis-porphyrin, cladribine, clomifene analogues, clotrimazole, collismycin A, collismycin B, combretastatin A4, combretastatin analogue, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, deslorelin, dexifosfamide, dexrazoxane, dexverapamil, diaziquone, didemnin B, didox, diethylnorspermine, dihydro-5-azacytidine, dihydrotaxol, 9-dihydrotaxol, dioxamycin, diphenyl spiromustine, discodermolide, docosanol, dolasetron, doxifluridine, droloxifene, dronabinol, duocarmycin SA, ebselen, ecomustine, edelfosine, edrecolomab, eflornithine, elemene, emitefur, epirubicin, epothilones, desoxyepothilones (A and B), epithilones, epristeride, estramustine analogue, estrogen agonists, estrogen antagonists, androgen antagonists, etanidazole, etoposide, etoposide 4'-phosphate, exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, gelatinase inhibitors, glutathione inhibitors, hepsulfam, heregulin, hexamethylene bisacetamide, hypericin, ibandronic acid, idarubicin, idoxifene, idramantone, ilmofosine, ilomastat, imidazoacridones, imiquimod, immunostimulant peptides, insulin-like growth factor-1 receptor inhibitor, interferon agonists, interferons, interleukins, iobenguane, iododoxorubicin, 4-ipomeanol, irinotecan, iroplact, irsogladine, isobengazole, isohomohalicondrin B, itasetron, jasplakinolide, kahalalide F, lamellarin-N triacetate, lanreotide, leinamycin, lenograstim, lentinan sulfate, leptolstatin, letrozole, leukemia inhibiting factor, leukocyte alpha interferon, leuprolide+estrogen+progesterone, leuprorelin, levamisole, liarozole, lipophilic platinum compounds, lissoclinamide 7, lobaplatin, lombricine, lometrexol, lonidamine, losoxantrone, lovastatin, loxoribine, lurtotecan, lutetium texaphyrin, lysofylline, maitansine, mannostatin A, marimastat, masoprocol, matrilysin inhibitors, matrix metalloproteinase inhibitors, menogaril, merbarone, 2-Me-D-Trp(6),desgly(10)-lhrh ethylamide (Meterelin™), methioninase, metoclopramide, macrophage migration inhibitory factor (MIF) inhibitor, mifepristone, miltefosine, mirimostim, plicamycin (Mithracin™), mitoguazone, mitolactol, mitomycin analogues, mitonafide, mitotoxin fibroblast growth factor-saporin, mitoxantrone, mofarotene, molgramostim, monoclonal antibody, human chorionic gonadotrophin, monophosphoryl lipid A+myobacterium cell wall SK, mopidamol, multiple drug resistance gene inhibitor, mustard anticarcinoma agents, mycaperoxide B, mycobacterial cell wall extract, myriaporone, N-acetyldinaline, N-substituted benzamides, nafarelin, nagrestip, naloxone+pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, O6-benzylguanine, octreotide, okicenone, onapristone, ondansetron, oracin, ormaplatin, osaterone, oxaliplatin, oxaunomycin, paclitaxel analogues, paclitaxel derivatives, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, perillyl alcohol, phenazinomycin, phenyl acetate, phosphatase inhibitors, picibanil, pilocarpine hydrochloride, pirarubicin, piritrexim, placetin A, placetin B, plasminogen activator inhibitor, platinum-triamine complex, podophyllotoxin, porfimer sodium, porfiromycin, propyl bis-acridone, prostaglandin J2, proteasome inhibitors, protein A-based immune modulator, protein kinase C inhibitors, microalgal, protein tyrosine phosphatase inhibitors, purine nucleoside phosphorylase inhibitors, purpurins, pyrazoloacridine, pyridoxylated hemoglobin polyoxyethylene conjugate, raf antagonists, ramosetron, ras farnesyl protein transferase inhibitors, ras inhibitors, ras-GAP inhibitor, retelliptine demethylated, rhenium (Re) 186 etidronate, rhizoxin, ribozymes, RH retinamide, rogletimide, rohitukine, romurtide, roquinimex, rubiginone B1, ruboxyl, safingol, saintopin, 2-chloroethyl-3-sarcosinamide-1-nitrosourea (SarCNU), sarcophytol A, sargramostim, Sdi 1 mimetics, semustine, senescence derived inhibitor 1, single chain antigen binding protein, sizofiran, sobuzoxane, sodium borocaptate, sodium phenylacetate, solverol, somatomedin binding protein, sonermin, sparfosic acid, spicamycin D, splenopentin, spongistatin 1, squalamine, stipiamide, stromelysin inhibitors, sulfinosine, superactive vasoactive intestinal peptide antagonist, suradista, suramin, swainsonine, synthetic glycosaminoglycans, tallimustine, tamoxifen methiodide, tauromustine, tazarotene, tecogalan sodium, tegafur, tellurapyrylium, telomerase inhibitors, temoporfin, temozolomide, teniposide, tetrachlorodecaoxide, tetrazomine, thaliblastine, thalidomide, thiocoraline, thrombopoietin, thrombopoietin mimetic, thymalfasin, thymopoietin receptor agonist, thymotrinan, thyroid stimulating hormone, tin ethyl etiopurpurin, tirapazamine, titanocene dichloride, topotecan, topsentin, toremifene, totipotent stem cell factor, tretinoin, triacetyluridine, triciribine, triptorelin, tropisetron, turosteride, tyrosine kinase inhibitors, tyrphostins, ubiquitin C (UBC) inhibitors, ubenimex, urogenital sinus-derived growth inhibitory factor, urokinase receptor antagonists, vapreotide, variolin B, velaresol, veramine, verdins, verteporfin, vinorelbine, vinxaltine, vitaxin, vorozole, and combinations thereof.

27. A method for treating a proliferative disorder comprising administering to a subject in need thereof a formulation comprising occidiofungin, and one or more cyclodextrins and an aqueous solvent in an amount effective to treat the proliferative disorder, wherein said formulation comprises either
   a) said occidiofungin in an amount ranging from about 20 g/mL to about 1 g/mL; or
   b) said one or more cyclodextrins at between about 0.5% to about 10% weight/volume (w/v) of said formulation, wherein said proliferative disorder is ovarian cancer or lymphoma.

28. The method according to claim 27, wherein said formulation comprises between about 0.5% to about 10% weight/volume (w/v) of said one or more cyclodextrins.

29. The method according to claim 27, wherein said formulation comprises said occidiofungin in an amount ranging from about 20 µg/mL to about 1 g/mL.

30. The method according to claim 27, wherein said one or more cyclodextrins is selected from the group consisting of α-cyclodextrin, β-cyclodextrin, γ-cyclodextrin, cyclomaltonose, variants thereof, and any combination thereof.

31. The method according to claim 30, wherein said one or more cyclodextrins is selected from the group consisting of hydroxypropyl-β-cyclodextrin, sulfobutylether-β-cyclodextrin, hydroxyethyl β-cyclodextrin, methyl-β-cyclodextrin, dimethyl-β-cyclodextrin, randomly dimethylated-β-cyclodextrin, randomly methylated-β-cyclodextrin, carboxymethyl-β-cyclodextrin, carboxymethyl ethyl-β-cyclodextrin, diethyl-β-cyclodextrin, tri-O-methyl-β-cyclodextrin, tri-O-ethyl-β-cyclodextrin, tri-O-butyryl-β-cyclodextrin, tri-O-valeryl-γ-cyclodextrin, di-O-hexanoyl-β-cyclodextrin, glucosyl-β-cyclodextrin, maltosyl-β-cyclodextrin, and 2-hydroxy-3-trimethyl-ammoniopropyl-β-cyclodextrin, or combinations thereof.

32. The method according to claim 27, wherein said one or more cyclodextrins is hydroxypropyl-β-cyclodextrin.

33. The method according to claim 27, wherein said formulation further comprises lipid vesicles.

34. The method according to claim 33, wherein said lipid vesicles comprise lipids selected from the group consisting of 1,2-Dioleoyl-sn-glycero-3-phosphocholine, 1,2-dipalmitoyl-sn-glycero-3-[phospho-rac-(3-lysyl(1-glycerol))], and combinations thereof.

35. The method according to claim 27, wherein said aqueous solvent is a pharmaceutically acceptable buffer, excipient, or combination thereof.

36. The method according to claim 35, wherein said pharmaceutically acceptable buffer, excipient, or combination thereof is selected from the group consisting of Ringer's solution, isotonic saline, isotonic glucose solutions, distilled water, and phosphate buffered saline.

37. The method according to claim 27, further comprising administering to the subject in need thereof at least one chemotherapeutic agent in an amount effective to treat said ovarian cancer or lymphoma.

38. The method according to claim 37, wherein said at least one chemotherapeutic agent is selected from the group consisting of:
   analogs of gonadotropin releasing hormone;
   nitrosoureas, 1-(4-amino-2-methyl-5-pyrimidinyl)methyl-3-(2-chloroethyl)-3-nitrosourea (ACNU), 1,3-bis (2-chloroethyl)-1-nitroso-urea (BCNU), 1-(2-chloroethyl)-3-cyclohexyl-1-nitrosourea (CCNU), N-hydroxyethylnitroso-N'-chloroethylurea (HCNU);
   cytostatic antibiotics, doxorubicin, pegylated liposomal doxorubicin, 5-fluorodeoxyuridine, 5-fluoro-2'-deoxyuridine 5'-monophosphate (5-FdUMP), 5-fluorouracil, 5-fluorouridine, procarbazine, docetaxel, gemcitabine, gemcitabine hydrochloride, telozolomide, epirubicin, epirubicin hydrochloride, idarubicin hydrochloride, zorubicin hydrochloride, aclarubicin, amrubicin, nemorubicin, pirarubicin;
   vinca alkaloids, vinblastine, vincristine, vindesine; and
   acivicin, acodazole hydrochloride, acronine, ambomycin, ametantrone acetate, aminoglutethimide, anthramycin, asparaginase, asperlin, bevacizumab (Avastin™), azacitidine, azetepa, azotomycin, benzodepa, bisantrene hydrochloride, bisnafide dimesylate, bleomycin sulfate, brequinar sodium, busulfan, cactinomycin, calusterone, caracemide, carbetimer, carboplatin, carmustine, carubicin hydrochloride, cedefingol, cetuximab, chlorambucil, cirolemycin, cisplatin, crisnatol mesylate, cyclophosphamide, cytarabine, dacarbazine, N-[2-(dimethyl-amino)ethyl]acridine-4-carboxamide (DACA), dactinomycin, daunomycin, dexormaplatin, dezaguanine, dezaguanine mesylate, droloxifene citrate, dromostanolone propionate, duazomycin, edatrexate, eflornithine hydrochloride, elsamitrucin, enoplatin, enpromate, epipropidine, erbulozole, erlotinib, esorubicin hydrochloride, estramustine, estramustine phosphate sodium, ethiodized oil $I^{131}$, etoposide phosphate, etoprine, fadrozole hydrochloride, fludarabine phosphate, flurocitabine, fosquidone, fostriecin sodium, gefitinib (Iressa™), gold (Au) 198, hydroxyurea, ifosfamide, imatinib mesylate, interferon alfa-2a, interferon alfa-2b, interferon alfa-n1, interferon alfa-n3, interferon beta-I a, interferon gamma-I b, iproplatin, irinotecan hydrochloride, lanreotide acetate, leuprolide acetate, liarozole hydrochloride, lometrexol sodium, lomustine, losoxantrone hydrochloride, maytansine, mechlorethamine hydrochloride, megestrol acetate, melengestrol acetate, melphalan, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, oxisuran, paclitaxel, peliomycin, pentamustine, peplomycin sulfate, pipobroman, piposulfan, piroxantrone hydrochloride, plicamycin, plomestane, prednimustine, procarbazine hydrochloride, puromycin, puromycin hydrochloride, pyrazofurin, riboprine, rituximab, safinol, safingol hydrochloride, simtrazene, sparfosate sodium, sparsomycin, spirogermanium hydrochloride, spiromustine, spiroplatin, streptonigrin, streptozocin, strontium 89 (Sr) chloride, sulofenur, talisomycin, tamoxifen, taxane, taxoid, teloxantrone hydrochloride, teroxirone, testolactone, thiamiprine, thioguanine, thiotepa, nolatrexed (Thymitaq™), tiazofurin, raltitrexed (Tomudex™), 4beta-aminoalkyl-4'-O-demethyl-4-desoxypodophyllotoxin (TOP-53), topotecan hydrochloride: toremifene citrate, trastuzumab, trestolone acetate, triciribine phosphate, trimetrexate, trimetrexate glucuronate, tubulozole hydrochloride, uracil mustard, uredepa, vinblastine sulfate, vincristine sulfate, vindesine sulfate, vinepidine sulfate, vinglycinate sulfate, vinleurosine sulfate, vinorelbine tartrate, vinrosidine sulfate, vinzolidine sulfate, zeniplatin, zinostatin, 2-chlorodeoxyadenosine, 2'-deoxformycin, 9-aminocamptothecin, raltitrexed, N-propargyl-5,8-dideazafolic acid, 2-chloro-2'-arabino-fluoro-2'-deoxyadenosine, 2-chloro-2'-deoxyadenosine, anisomycin, trichostatin A, hPRL-G129R, CEP-751, linomide, 20-epi-1,25 dihydroxyvitamin D3, 5-ethynyluracil, abiraterone, acylfulvene, adecypenol, adozelesin, aldesleukin, ALL-tyrosine kinase (TK) antagonists, altretamine, ambamustine, amidox, amifostine, aminolevulinic acid, amsacrine, anagrelide, anastrozole, andrographolide, antagonist D, antagonist G, teverelix (Antarelix™), anti-dorsalizing morphogenetic protein-1, antineoplaston, aphidicolin glycinate, apoptosis gene modulators, apoptosis regulators, apurinic acid, 1-beta-D-Arabinofuranosylcytosine 5'-diphosphate-rac-1-S-octadecyl-2-O-palmitoyl-1-thioglycerol (ara-CDP-DL-PTBA), arginine deaminase, asulacrine, atamestane, atrimustine, axinastatin 1, axinastatin 2, axinastatin 3, azasetron, azatoxin, azatyrosine, baccatin III derivatives, balanol, batimastat, breakpoint cluster region/abelson murine leukemia viral oncogene homolog 1 (BCR/ABL) antagonists, benzochlorins, benzoylstaurosporine, beta lactam derivatives, beta-alethine, betaclamycin B, betulinic acid, basic fibroblast growth factor (bFGF) inhibitor, bicalutamide, bisaziridinylspermine, bisnafide, bistratene A, bizelesin, breflate, bropirimine, budotitane, buthionine sulfoximine, calcipotriol, calphostin C, camptothecin derivatives, canarypox IL-2, capecitabine, carboxamide-amino-triazole, carboxyamidotriazole, CaRest M3™, CARN 700, carzelesin, castanospermine, cecropin B, cetrorelix, chlorins, chloroquinoxaline sulfonamide, cicaprost, cis-porphyrin, cladribine, clomifene analogues, clotrimazole, collismycin A, collismycin B, combretastatin A4, combretastatin analogue, conagenin, crambescidin 816, crisnatol, cryptophycin 8, curacin A, cyclopentanthraquinones, cycloplatam, cypemycin, cytarabine ocfosfate, cytolytic factor, cytostatin, dacliximab, decitabine, dehydrodidemnin B, deslorelin, dexifosfamide, dexrazoxane, dexverapamil, diaziquone, didemnin B, didox, diethylnorspermine, dihydro-5-azacytidine, dihydrotaxol, 9-dihydrotaxol, dioxamycin, diphenyl spiromustine, discodermolide, docosanol, dolasetron, doxifluridine, droloxifene, dronabinol, duocarmycin SA, ebselen, ecomustine, edelfosine, edrecolomab, eflornithine, elemene, emitefur, epothilones, desoxyepothilones (A and B), epithilones, epristeride, estramustine analogue, estrogen agonists, estrogen antagonists, androgen antagonists, etanidazole, etoposide, etoposide 4'-phosphate, exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, gelatinase inhibitors, glutathione inhibitors, hepsulfam, heregulin, hexamethylene bisacetamide, hypericin, ibandronic acid, idarubicin, idoxifene, idramantone, ilmofosine, ilomastat, imidazoacridones, imiquimod, immunostimulant peptides, insulin-like growth factor-1 receptor inhibitor, interferon agonists, iobenguane, iododoxorubicin, 4-ipomeanol, irinotecan, iroplact, irsogladine, isobengazole, isohomohalicondrin B, itasetron, jasplakinolide, kahalalide F, lamellarin-N triacetate, lanreotide, leinamycin, lenograstim, lentinan sulfate, leptolstatin, letrozole, leukocyte alpha interferon, leuprolide+estrogen+progesterone, leuprorelin, levamisole, liarozole, lipophilic platinum compounds, lissoclinamide 7, lobaplatin, lombricine, lometrexol, lonidamine, losoxantrone, lovastatin, loxoribine, lurtotecan, lutetium texaphyrin, lysofylline, maitansine, mannostatin A, marimastat, masoprocol, matrilysin inhibitors, matrix metalloproteinase inhibitors, menogaril, merbarone, 2-Me-D-Trp(6),desgly (10)-lhrh ethylamide (Meterelin™), methioninase, metoclopramide, macrophage migration inhibitory factor (MIF) inhibitor, mifepristone, miltefosine, mirimostim, plicamycin (Mithracin™), mitoguazone, mitolactol, mitomycin analogues, mitonafide, mitotoxin fibroblast growth factor-saporin, mitoxantrone, mofarotene, molgramostim, monophosphoryl lipid A+myobacterium cell wall SK, mopidamol, mustard anticarcinoma agents, mycaperoxide B, myriaporone, N-acetyldinaline, N-substituted benzamides, nafarelin, nagrestip, naloxone+pentazocine, napavin, naphterpin, nartograstim, nedaplatin, neridronic acid, nilutamide, nisamycin, nitric oxide modulators, nitroxide antioxidant, nitrullyn, O6-benzylguanine, octreotide, okicenone, onapristone, ondansetron, oracin, ormaplatin, osaterone, oxaliplatin, oxaunomycin, paclitaxel analogues, paclitaxel derivatives, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, perillyl alcohol, phenazinomycin, phenylacetate, picibanil, pilocarpine hydrochloride, piritrexim, placetin A, placetin B, plasminogen activator inhibitor, platinum-triamine complex, podophyllotoxin, porfimer sodium, porfiromycin, propyl bis-acridone, prostaglandin J2, protein A-based immune modulator, protein kinase C inhibitors, microalgal, protein tyrosine phosphatase inhibitors, purine nucleoside phosphorylase inhibitors, purpurins, pyrazoloacridine, pyridoxylated hemoglobin polyoxyethylene conjugate, raf antagonists, ramosetron, ras farnesyl protein transferase inhibitors, ras inhibitors, ras-GAP inhibitor, retelliptine demethylated, rhenium (Re) 186 etidronate, rhizoxin, RII retinamide, rogletimide, rohitukine, romurtide, roquinimex, rubiginone B1, ruboxyl, safingol, saintopin, 2-chloroethyl-3-sarcosinamide-1-nitrosourea (SarCNU), sarcophytol A, sargramostim, Sdi 1 mimetics, semustine, senescence derived inhibitor 1, sizofiran, sobuzoxane, sodium borocaptate, sodium phenylacetate, solverol, sonermin, sparfosic acid, spicamycin D, splenopentin, spongistatin 1, squalamine, stipiamide, stromelysin inhibitors, sulfinosine, superactive vasoactive intestinal peptide antagonist, suradista, suramin, swainsonine, synthetic glycosaminoglycans, tallimustine, tamoxifen methiodide, tauromustine, tazarotene, tecogalan sodium, tegafur, tellurapyrylium, telomerase inhibitors, temoporfin, temozolomide, teniposide, tetrachlorodecaoxide, tetrazomine, thaliblastine, thalidomide, thiocoraline, thrombopoietin, thrombopoietin mimetic, thymalfasin, thymopoietin receptor agonist, thymotrinan, thyroid stimulating hormone, tin ethyl etiopurpurin, tirapazamine, titanocene dichloride, topotecan, topsentin, toremifene, totipotent stem cell factor, tretinoin, triacetyluridine, triciribine, triptorelin, tropisetron, turosteride, tyrphostins, ubiquitin C (UBC) inhibitors, ubenimex, urogenital sinus-derived growth inhibitory factor, urokinase receptor antagonists, vapreotide, variolin B, velaresol, veramine, verdins, verteporfin, vinorelbine, vinxaltine, vitaxin, vorozole, and combinations thereof.

39. The method according to claim 37, wherein said method comprises the sequential administration of said formulation and said at least one chemotherapeutic agent.

40. The method according to claim 27, wherein the subject in need thereof is a mammal.

41. The method according to claim 40, wherein said mammal is a non-human animal.

42. The method according to claim 41, wherein said non-human animal is a rodent, chimpanzee, monkey, or dog.

43. The method according to claim 40, wherein said mammal is a human.

44. The method according to claim 37, wherein said at least one chemotherapeutic agent is selected from the group consisting of:
analogs of gonadotropin releasing hormone;
nitrosoureas, 1-(4-amino-2-methyl-5-pyrimidinyl) methyl-3-(2-chloroethyl)-3-nitrosourea (ACNU), 1,3-bis (2-chloroethyl)-1-nitroso-urea (BCNU), 1-(2-chloroethyl)-3-cyclohexyl-1-nitrosourea (CCNU), N-hydroxyethylnitroso-N'-chloroethylurea (HCNU);
cytostatic antibiotics, doxorubicin, pegylated liposomal doxorubicin, 5-fluorodeoxyuridine, 5-fluoro-2'-deoxyuridine 5'-monophosphate (5-FdUMP), 5-fluorouracil, 5-fluorouridine, procarbazine, docetaxel, gemcitabine, gemcitabine hydrochloride, telozolomide;
vinca alkaloids, vinblastine, vincristine, vindesine; and
acivicin, acodazole hydrochloride, acronine, ambomycin, ametantrone acetate, aminoglutethimide, anthramycin, asparaginase, asperlin, bevacizumab (Avastin™), azacitidine, azetepa, azotomycin, benzodepa, bisantrene hydrochloride, bisnafide dimesylate, bleomycin sulfate, brequinar sodium, busulfan, cactinomycin, calusterone, caracemide, carbetimer, carboplatin, carmustine, carubicin hydrochloride, cedefingol, cetuximab, chlorambucil, cirolemycin, cisplatin, crisnatol mesylate, cyclophosphamide, cytarabine, dacarbazine, N-[2-(dimethyl-amino)ethyl]acridine-4-carboxamide (DACA), dactinomycin, daunomycin, dexormaplatin, dezaguanine, dezaguanine mesylate, droloxifene citrate, dromostanolone propionate, duazomycin, edatrexate, eflornithine hydrochloride, elsamitrucin, enloplatin, enpromate, epipropidine, epirubicin hydrochloride, erbulozole, erlotinib, esorubicin hydrochloride, estramustine, estramustine phosphate sodium, ethiodized oil I$^{131}$, etoposide phosphate, etoprine, fadrozole hydrochloride, fludarabine phosphate, flurocitabine, fosquidone, fostriecin sodium, gefitinib (Iressa™), gold (Au) 198, hydroxyurea, idarubicin hydrochloride, ifosfamide, imatinib mesylate, interferon alfa-2a, interferon alfa-2b, interferon alfa-n1, interferon alfa-n3, interferon beta-I a, interferon gamma-I b, iproplatin, irinotecan hydrochloride, lanreotide acetate, leuprolide acetate, liarozole hydrochloride, lometrexol sodium, lomustine, losoxantrone hydrochloride, maytansine, mechlorethamine hydrochloride, megestrol acetate, melengestrol acetate, melphalan, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, oxisuran, paclitaxel, peliomycin, pentamustine, peplomycin sulfate, pipobroman, piposulfan, piroxantrone hydrochloride, plicamycin, plomestane, prednimustine, procarbazine hydrochloride, puromycin, puromycin hydrochloride, pyrazofurin, riboprine, rituximab, safinol, safingol hydrochloride, simtrazene, sparfosate sodium, sparsomycin, spirogermanium hydrochloride, spiromustine, spiroplatin, streptonigrin, streptozocin, strontium (Sr) chloride 89, sulofenur, talisomycin, tamoxifen, taxane, taxoid, teloxantrone hydrochloride, teroxirone, testolactone, thiamiprine, thioguanine, thiotepa, nolatrexed (Thymitaq™), tiazofurin, raltitrexed (Tomudex™), 4beta-aminoalkyl-4'-O-demethyl-4-desoxypodophyllotoxin (TOP-53), topotecan hydrochloride: toremifene citrate, trastuzumab, trestolone acetate, triciribine phosphate, trimetrexate, trimetrexate glucuronate, tubulozole hydrochloride, uracil mustard, uredepa, vinblastine sulfate, vincristine sulfate, vindesine sulfate, vinepidine sulfate, vinglycinate sulfate, vinleurosine sulfate, vinorelbine tartrate, vinrosidine sulfate, vinzolidine sulfate, zeniplatin, zinostatin, zorubicin hydrochloride, 2-chlorodeoxyadenosine, 2'-deoxformycin, 9-aminocamptothecin, raltitrexed, N-propargyl-5,8-dideazafolic acid, 2-chloro-2'-arabino-fluoro-2'-deoxyadenosine, 2-chloro-2'-deoxyadenosine, anisomycin, trichostatin A, hPRL-G129R, CEP-751, linomide, 20-epi-1,25 dihydroxyvitamin D3, 5-ethynyluracil, abiraterone, aclarubicin, acylfulvene, adecypenol, adozelesin, aldesleukin, ALL-tyrosine kinase (TK) antagonists, altretamine, ambamustine, amidox, amifostine, aminolevulinic acid, amrubicin, amsacrine, anagrelide, anastrozole, andrographolide, antagonist D, antagonist G, teverelix (Antarelix™), anti-dorsalizing morphogenetic protein-1, antineoplaston, aphidicolin glycinate, apoptosis gene modulators, apoptosis regulators, apurinic acid, 1-beta-D-Arabinofuranosylcytosine 5'-diphosphate-rac-1-S-octadecyl-2-O-palmitoyl-1-thioglycerol (ara-CDP-DL-PTBA), arginine deaminase, asulacrine, atamestane, atrimustine, axinastatin 1, axinastatin 2, axinastatin 3, azasetron, azatoxin, azatyrosine, baccatin III derivatives, balanol, batimastat, breakpoint cluster region/abelson murine leukemia viral oncogene homolog 1 (BCR/ABL) antagonists, benzochlorins, benzoyl staurosporine, beta lactam derivatives, beta-alethine, betaclamycin B, betulinic acid, basic fibroblast growth factor (bFGF) inhibitor, bicalutamide, bisaziridinylspermine, bisnafide, bistratene A, bizelesin, breflate, bropirimine, budotitane, buthionine sulfoximine, calcipotriol, calphostin C, camptothecin derivatives, canarypox IL-2, capecitabine, carboxamide-amino-triazole, carboxyamidotriazole, CaRest M3™, CARN 700, cartilage derived inhibitor, carzelesin, casein kinase inhibitors (ICOS), castanospermine, cecropin B, cetrorelix, chlorins, chloroquinoxaline sulfonamide, cicaprost, cis-porphyrin, cladribine, clomifene analogues, clotrimazole, collismycin A, collismycin B, combretastatin A4, combretastatin analogue, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, deslorelin, dexifosfamide, dexrazoxane, dexverapamil, diaziquone, didemnin B, didox, diethylnorspermine, dihydro-5-azacytidine, dihydrotaxol, 9-dihydrotaxol, dioxamycin, diphenyl spiromustine, discodermolide, docosanol, dolasetron, doxifluridine, droloxifene, dronabinol, duocarmycin SA, ebselen, ecomustine, edelfosine, edrecolomab, eflornithine, elemene, emitefur, epirubicin, epothilones, desoxyepothilones (A and B), epithilones, epristeride, estramustine analogue, estrogen agonists, estrogen antagonists, androgen antagonists, etanidazole, etoposide, etoposide 4'-phosphate, exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, gelatinase inhibitors, glutathione inhibitors, hepsulfam, heregulin, hexamethylene bisacetamide, hypericin, ibandronic acid, idarubicin, idoxifene, idramantone, ilmofosine, ilomastat, imidazoacridones, imiquimod, immunostimulant peptides, insulin-like growth factor-1 receptor inhibitor, interferon agonists, interferons, interleukins, iobenguane, iododoxorubicin, 4-ipomeanol, irinotecan, iroplact, irsogladine, isobengazole, isohomohalicondrin B, itasetron, jasplakinolide, kahalalide F, lamellarin-N triacetate, lanreotide, leinamycin, lenograstim, lentinan sulfate, leptolstatin, letrozole, leukemia inhibiting factor, leukocyte alpha interferon, leuprolide+estrogen+progesterone, leuprorelin, levamisole, liarozole, lipophilic platinum compounds, lissoclinamide 7, lobaplatin, lombricine, lometrexol, lonidamine, losoxantrone, lovastatin, loxoribine, lurtotecan, lutetium texaphyrin, lysofylline, maitansine, mannostatin A, marimastat, masoprocol, matrilysin inhibitors, matrix metalloproteinase inhibitors, menogaril, merbarone, 2-Me-D-Trp(6),desgly(10)-lhrh ethylamide (Meterelin™), methioninase, metoclopramide, macrophage migration inhibitory factor (MIF) inhibitor, mifepristone, miltefosine, mirimostim, plicamycin (Mithracin™), mitoguazone, mitolactol, mitomycin analogues, mitonafide, mitotoxin fibroblast growth factor-saporin, mitoxantrone, mofarotene, molgramostim, monoclonal antibody, human chorionic gonadotrophin, monophosphoryl lipid A+myobacterium cell wall SK, mopidamol, multiple drug resistance gene inhibitor, mustard anticarcinoma agents, mycaperoxide B, mycobacterial cell wall extract, myriaporone, N-acetyldinaline, N-substituted benzamides, nafarelin, nagrestip, naloxone+pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, O6-benzylguanine, octreotide, okicenone, onapristone, ondansetron, oracin, ormaplatin, osaterone, oxaliplatin, oxaunomycin, paclitaxel analogues, paclitaxel derivatives, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, perillyl alcohol, phenazinomycin, phenyl acetate, phosphatase inhibitors, picibanil, pilocarpine hydrochloride, pirarubicin, piritrexim, placetin A, placetin B, plasminogen activator inhibitor, platinum-triamine complex, podophyllotoxin, porfimer sodium, porfiromycin, propyl bis-acridone, prostaglandin J2, proteasome inhibitors, protein A-based immune modulator, protein kinase C inhibitors, microalgal, protein tyrosine phosphatase inhibitors, purine nucleoside phosphorylase inhibitors, purpurins, pyrazoloacridine, pyridoxylated hemoglobin polyoxyethylene conjugate, raf antagonists, ramosetron, ras farnesyl protein transferase inhibitors, ras inhibitors, ras-GAP inhibitor, retelliptine demethylated, rhenium (Re) 186 etidronate, rhizoxin, ribozymes, RH retinamide, rogletimide, rohitukine, romurtide, roquinimex, rubiginone B1, ruboxyl, safingol, saintopin, 2-chloroethyl-3-sarcosinamide-1-nitrosourea (SarCNU), sarcophytol A, sargramostim, Sdi 1 mimetics, semustine, senescence derived inhibitor 1, single chain antigen binding protein, sizofiran, sobuzoxane, sodium borocaptate, sodium phenylacetate, solverol, somatomedin binding protein, sonermin, sparfosic acid, spicamycin D, splenopentin, spongistatin 1, squalamine, stipiamide, stromelysin inhibitors, sulfinosine, superactive vasoactive intestinal peptide antagonist, suradista, suramin, swainsonine, synthetic glycosaminoglycans, tallimustine, tamoxifen methiodide, tauromustine, tazarotene, tecogalan sodium, tegafur, tellurapyrylium, telomerase inhibitors, temoporfin, temozolomide, teniposide, tetrachlorodecaoxide, tetrazomine, thaliblastine, thalidomide, thiocoraline, thrombopoietin, thrombopoietin mimetic, thymalfasin, thymopoietin receptor agonist, thymotrinan, thyroid stimulating hormone, tin ethyl etiopurpurin, tirapazamine, titanocene dichloride, topotecan, topsentin, toremifene, totipotent stem cell factor, tretinoin, triacetyluridine, triciribine, triptorelin, tropisetron, turosteride, tyrosine kinase inhibitors, tyrphostins, ubiquitin C (UBC) inhibitors, ubenimex, urogenital sinus-derived growth inhibitory factor, urokinase receptor antagonists, vapreotide, variolin B, velaresol, veramine, verdins, verteporfin, vinorelbine, vinxaltine, vitaxin, vorozole, and combinations thereof.

\* \* \* \* \*